(12) United States Patent
Russell

(10) Patent No.: US 7,942,785 B1
(45) Date of Patent: May 17, 2011

(54) JOINT RANGE OF MOTION MEASUREMENT DEVICE AND MOBILITY ENHANCER

(76) Inventor: Lori E. Russell, Reston, VA (US)

( * ) Notice: Subject to any disclaimer, the term of this patent is extended or adjusted under 35 U.S.C. 154(b) by 252 days.

(21) Appl. No.: 12/221,587

(22) Filed: Aug. 5, 2008

Related U.S. Application Data

(60) Provisional application No. 60/963,581, filed on Aug. 6, 2007.

(51) Int. Cl.
   *A63B 21/00* (2006.01)
(52) U.S. Cl. ............................................. 482/44; 482/49
(58) Field of Classification Search .................... 482/49, 482/44, 45, 148; 283/81, 101, 104; 220/503, 220/506, 428, 283; 600/587
   See application file for complete search history.

(56) References Cited

U.S. PATENT DOCUMENTS

| | | | |
|---|---|---|---|
| 3,645,413 A * | 2/1972 | Mitchell | 215/11.1 |
| 4,665,928 A | 5/1987 | Linial et al. | |
| 4,887,845 A * | 12/1989 | Nagai | 283/81 |
| 5,588,444 A | 12/1996 | Petragallo | |
| 5,758,658 A | 6/1998 | Petragallo | |
| 5,791,351 A | 8/1998 | Curchod | |
| 6,152,858 A | 11/2000 | Kolb | |
| 6,406,406 B1 | 6/2002 | Onorati | |
| 6,651,352 B2 | 11/2003 | McGorry et al. | |
| 6,709,017 B2 * | 3/2004 | Ross | 283/81 |

* cited by examiner

*Primary Examiner* — Jerome W Donnelly

(57) ABSTRACT

One embodiment of a multi-functional device for measuring joint range of motion of the wrist and forearm. In general, the embodiment includes a casing (20) containing fluid (23), and a plural number of calibration scale (24) assemblies. The casing (20) is sized appropriately to be gripped in a user's hand, and enables the user to obtain an assessment of his or her range of motion as various motions are performed. Specifically, the various motions made by the user while gripping the embodiment causes fluid (23) to shift inside of casing (20) as a reaction to the downward pull of gravity. The user obtains an instant visual measurement of joint range of motion by viewing the location of fluid (23) on the calibration scale (24) assemblies. The overall design empowers the user to measure his or her own range of motion, which engages him or her as he or she works to re-gain mobility, and provides a positive motivating influence. The device is also suitable for use when performing exercises and stretches. The device is intuitive, portable, and requires no medical training to use. Other embodiments are described and shown.

7 Claims, 19 Drawing Sheets

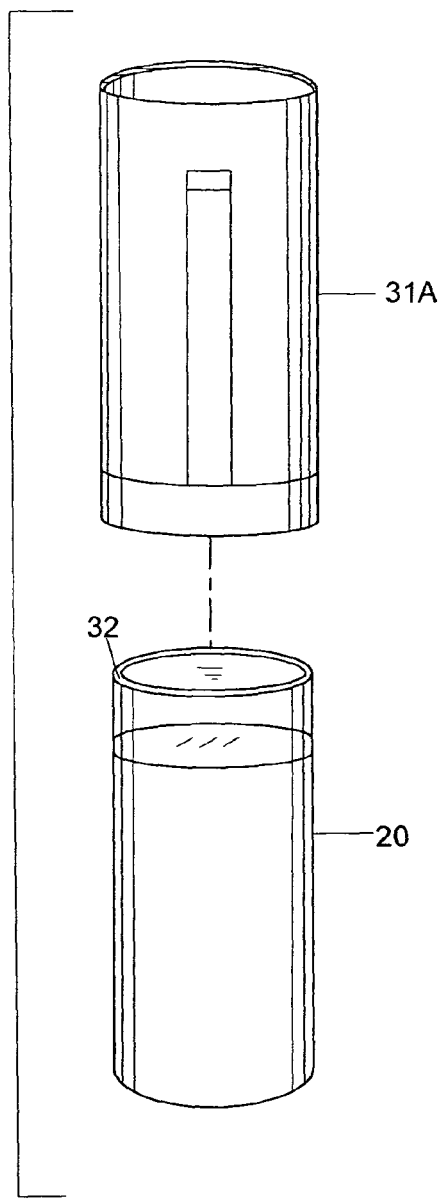
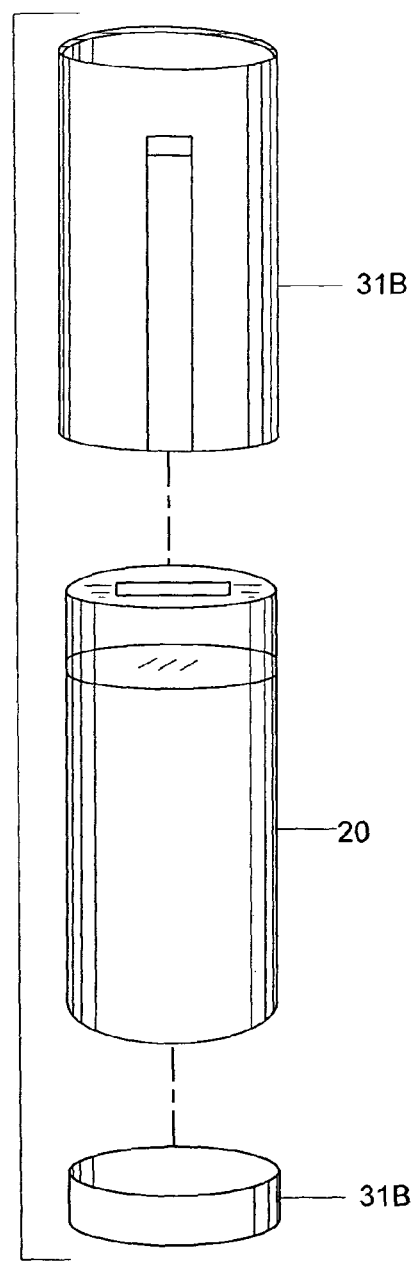
FIG. 11A
FIG. 11B

JOINT RANGE OF MOTION MEASUREMENT DEVICE AND MOBILITY ENHANCER

CROSS-REFERENCE TO RELATED APPLICATIONS

This application claims the benefit of PPA Ser. No. 60/963,581 filed 2007, Aug. 6 by the present inventor, which is incorporated by reference.

FEDERALLY SPONSORED RESEARCH

Not Applicable

SEQUENCE LISTING OR PROGRAM

Not applicable

FIELD OF THE INVENTION

This invention relates to devices that measure body movement, specifically to a multifunctional rehabilitative device and method for providing range of motion measurement, exercise, and/or stretching.

BACKGROUND OF THE INVENTION

Individuals may experience reduced ranges of motion in the various joints of the body as a result of physical injury or other infirmity. The quality of life of those individuals is adversely impacted due to the accompanying loss of physical function. This is especially true when the involved joints impact the use of the person's hands, wrists, and/or forearms, since so many daily tasks involve using them. Thus, bringing back the lost mobility is often a key goal of the individual.

If medical care is sought for help achieving this goal, medical practitioners often design therapeutic exercises to help the person overcome their limitations. Specifically, the therapeutic exercises are designed to rehabilitate the person by increasing the flexibility, strength, and endurance of the affected area.

Once the individual gains familiarity with the therapeutic exercises in the clinical setting, he or she is often asked to complete them at home. The home-based regimen often includes completing a set of several different exercises, typically 1-3 times a day.

This home-based regimen plays an important role in gaining back the lost range of motion. And, it requires the person to make a commitment to invest the time and energy in these exercises to achieve success.

It is this investment of time and energy, along with an overarching drive to gain back the use of their hand, wrist, and/or forearm, which leads the individual to want to assess their own rehabilitative status and progress.

Therefore, there is a strong need for a tool for self-assessment, to help inform and motivate the individual as he or she regains his or her joint range of motion, and consequently, his or her quality of life. It would be of increased benefit to the individual if the device were multifunctional, suitable for motivation, stretching, and/or exercise. The device of the present invention accomplishes this objective.

In the prior art, the joint range of motion measurement devices are designed for use in the clinical setting by trained medical professionals. Examples include compass-type angle indicators or goniometers, pendulum or bubble inclinometers, magnetic compass needles and the like. Although these devices find uses in the clinical setting, they suffer from a number of disadvantages.

First, their usage relies on the knowledge, skill, and experience of a trained medical practitioner and is therefore not well suited for personal private use.

Therefore, there is a need for a device that is simple in design and operation that does not require medical training to use.

Second, their usage occurs in the clinical setting, and is therefore only available to the person at appointment times. Thus, the measurements taken with the prior art devices are of limited motivating value for the individual. Specifically, the individual loses out on more frequent measurements, and the motivation such ongoing measurement can provide.

Therefore, there is a need for a device patients can use at their convenience to detect changes in their range of motion. This will ensure they receive the motivating benefits that ongoing measurement provides.

Third, their usage occurs while the patient remains relaxed and he or she plays no active role in the measurement. Therefore, since the patient is only passively involved, and not actively involved, he or she is less likely to fully understand where he or she is in terms of his or her progress.

Therefore, there is a need for a device patients can use where they are actively engaged in the range of motion measurement process.

Fourth, many prior art devices are expensive, and outside of typical consumers' price range since they are geared for clinical use.

Therefore, there is a need for a device that is not expensive.

Other disadvantages of prior art range of motion measurement devices include:

a) The need to involve someone other than the patient in the testing since many devices require more than one hand for positioning, stabilization, and operation.

b) Certain prior art inclinometer devices (e.g., the universal inclinometer or the bi-level inclinometer) require the patient to grip the devices' base, where the base does not have a shape conducive to providing a comfortable, secure, or repeatable grip.

c) One prior art device known as the wrist inclinometer is only capable of measuring supination and pronation. This limits the user's ability for measurement to just the frontal plane of the body (where supination and pronation occur).

d) Many prior art devices for range of motion measurement (e.g., goniometers, universal inclinometers) have problems with reproducibility and require the location of bony landmarks for proper positioning on the patient.

e) Prior art devices exclusively display measurements using degree increments, which provides useful measurement information, but may lack information that is easily interpreted by a patient.

For these reasons, the prior art devices for measuring joint motion are not well suited for patient home use. That is, the considerable cost and complexity associated with prior art prohibits their use for most consumers. Accordingly, a need exists for a device and method that can empower an individual to evaluate his or her rehabilitative status by assessing his or her joint range of motion. Ideally, the needed device is simple in design and operation, not costly, portable, and multifunctional.

From the known devices for exercise and stretching, there are many different options available, such as rope systems, springs, coils, dumbbells, etc. While these devices find uses, they have the drawback of not providing the user with any feedback on how he or she is progressing. For example, when a dumbbell is used as weight resistance, it is simply held in the user's hand, as dead weight. It does not provide the user with any insight into the rehabilitative process as exercises are performed.

Therefore, there is a need for a device and method that patients can use for exercise and stretching, that engages the user and provides insight into the rehabilitative process by simultaneously providing a visual indication of range of motion as the movements are performed.

The inventor of this device successfully used a self-built prototype during her recovery from a broken wrist.

SUMMARY OF INVENTION

The present invention refers to a multifunctional portable device for assessing the joint range of motion of the wrist and forearm. The device comprises a casing that contains a fluid, and that has a series of calibration scales visible on its surface. The fluid responds to the downward pull of gravity as the casing is moved by a user. Specifically, the calibration scales on the casing are configured to provide a user with a visual assessment of range of motion in real time as various motions are performed, as measured by the fluid's response to gravity in relation to the calibration scales. In addition to measuring joint range of motion, the unique design of the device makes it suitable for other rehabilitative uses such as an exercise and stretching.

DRAWINGS

Figures

In the drawings, related figures have the same number but different alphabetic suffixes. Some drawings include standard drafting symbol patterns for representing color. The colors used in the drawings are exemplary.

FIG. 11A and FIG. 11B show a front perspective view of another embodiment.

FIGS. 12A, 12B, 12C, and 12D show a front perspective view of alternative embodiments.

Figures 12A, 12B:
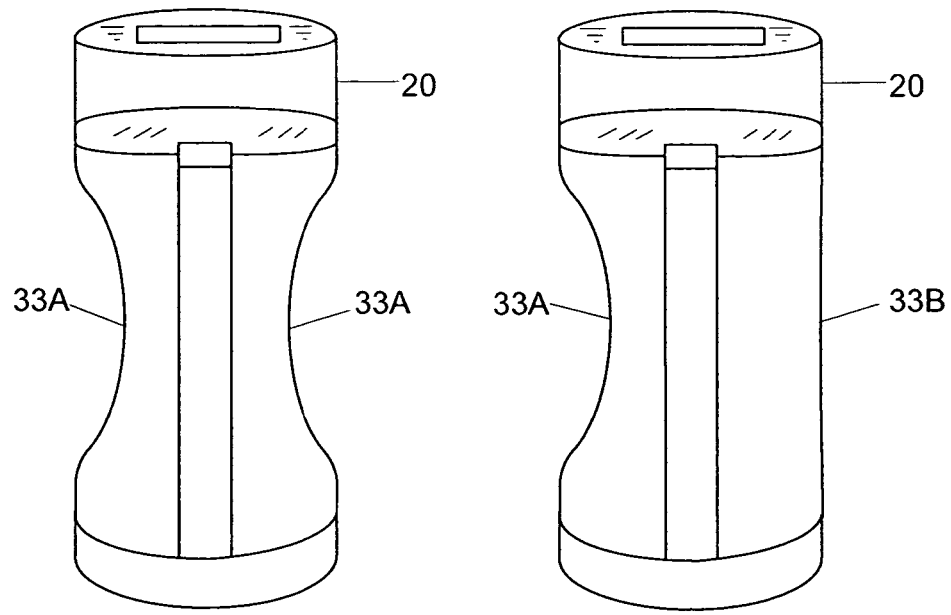
Figures 12C, 12D:
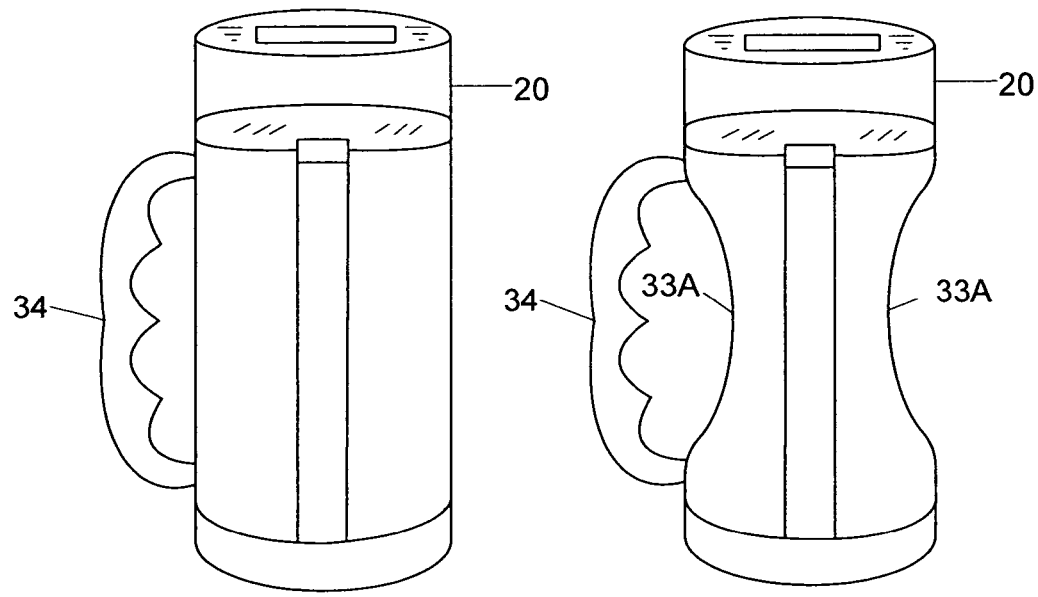
Figure 12E:
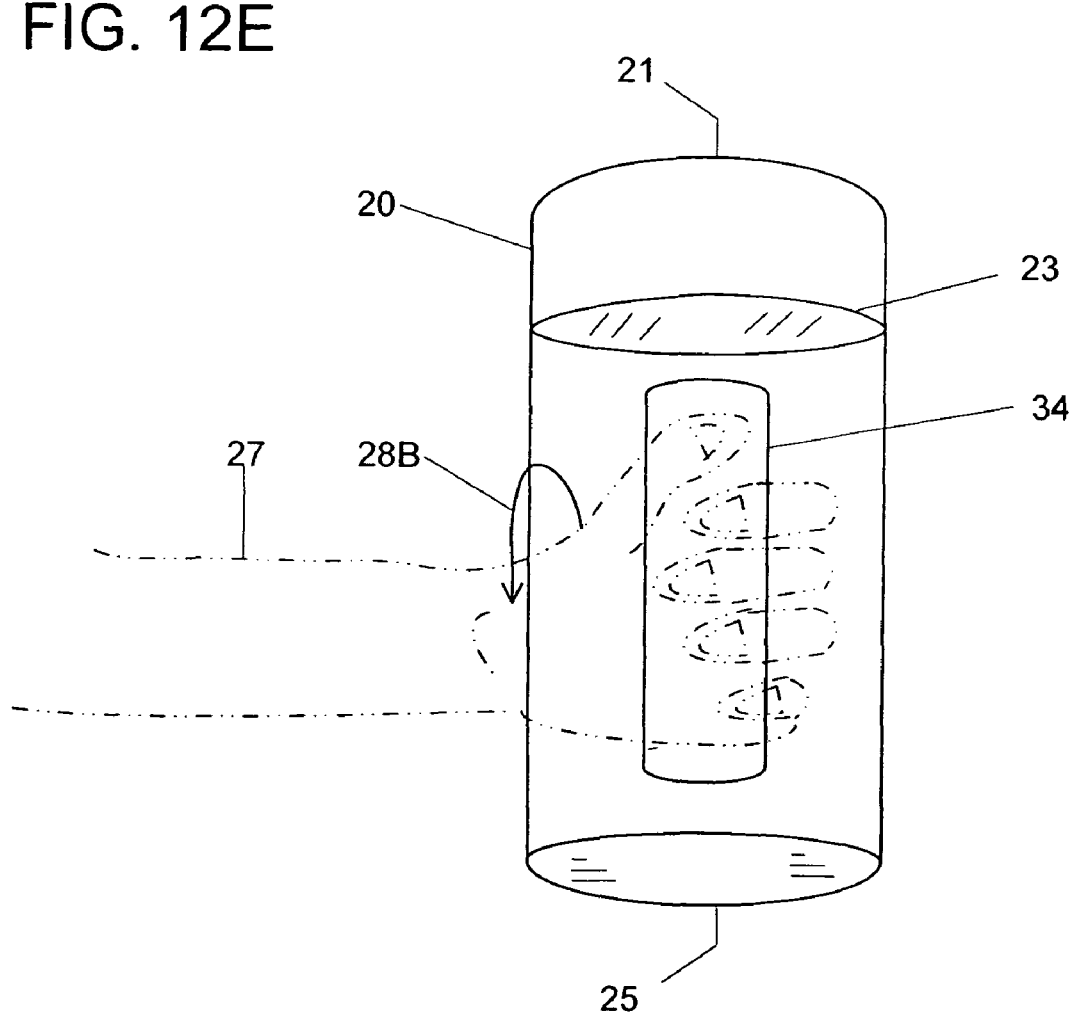

FIG. 12E shows a user side view of an alternative embodiment.

Figure 13:
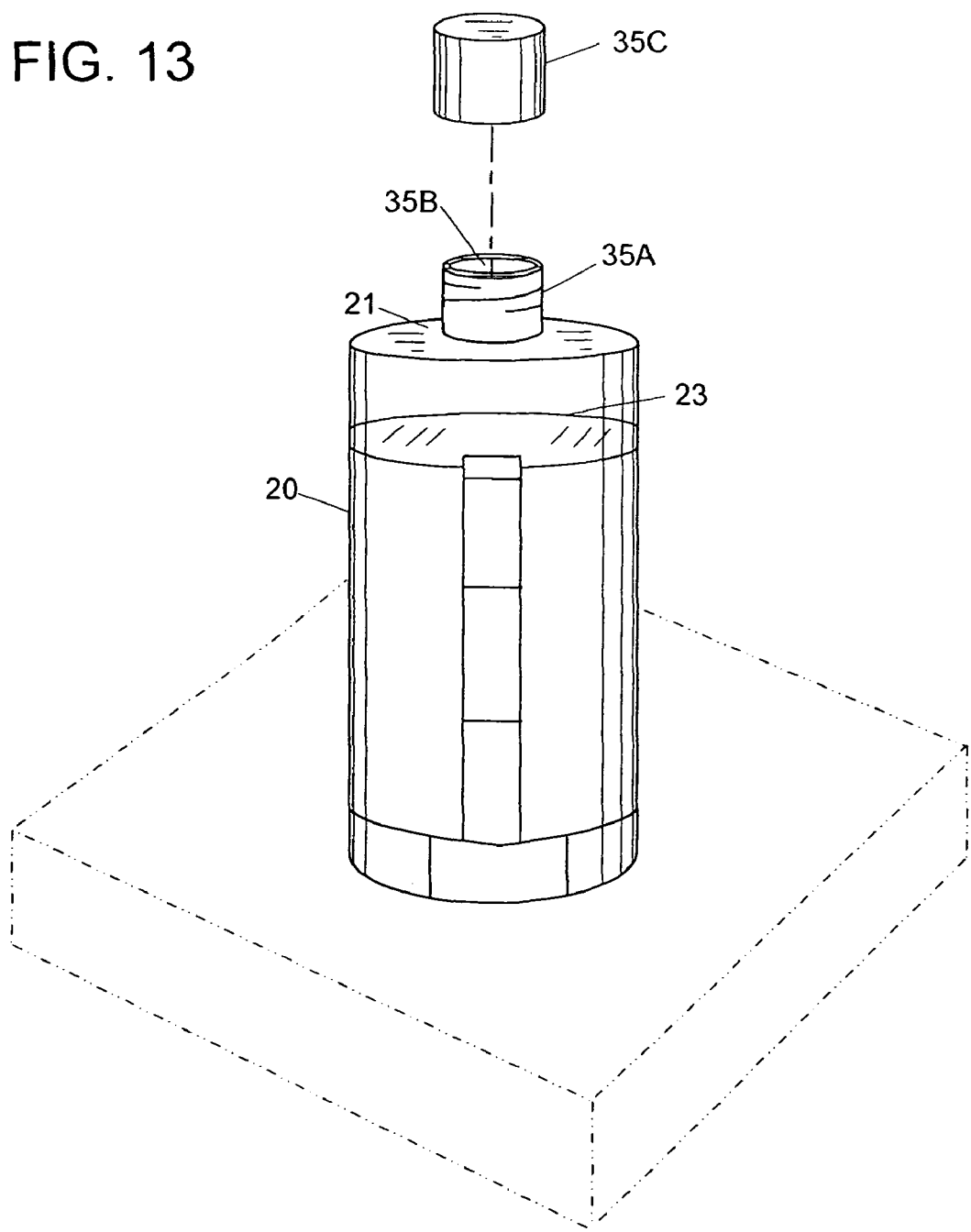

FIG. 13 shows a front perspective view of another embodiment.

Figure 14A:
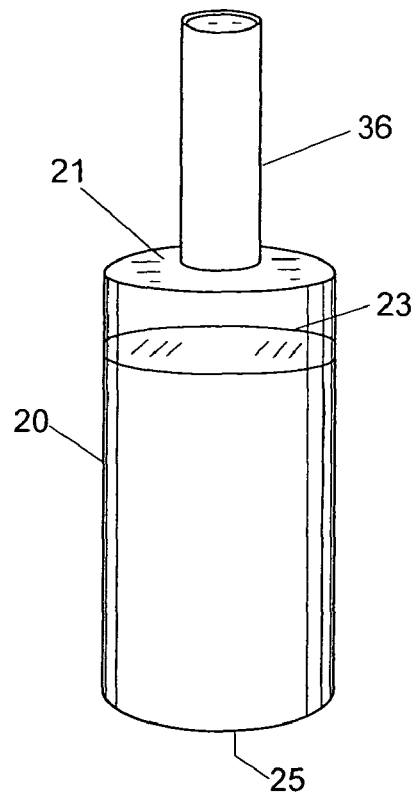

FIG. 14A shows a front perspective view of another embodiment.

Figure 14B:
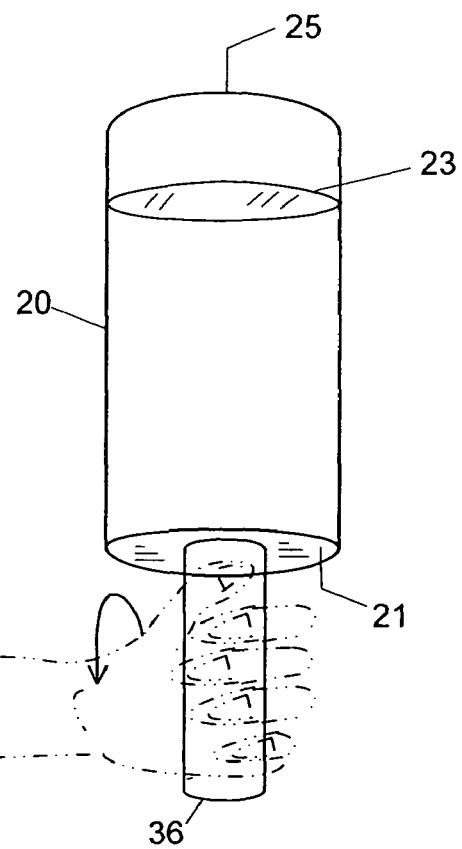

FIG. 14B shows a user side view with the subject's hand in a start position.

Figure 5A:
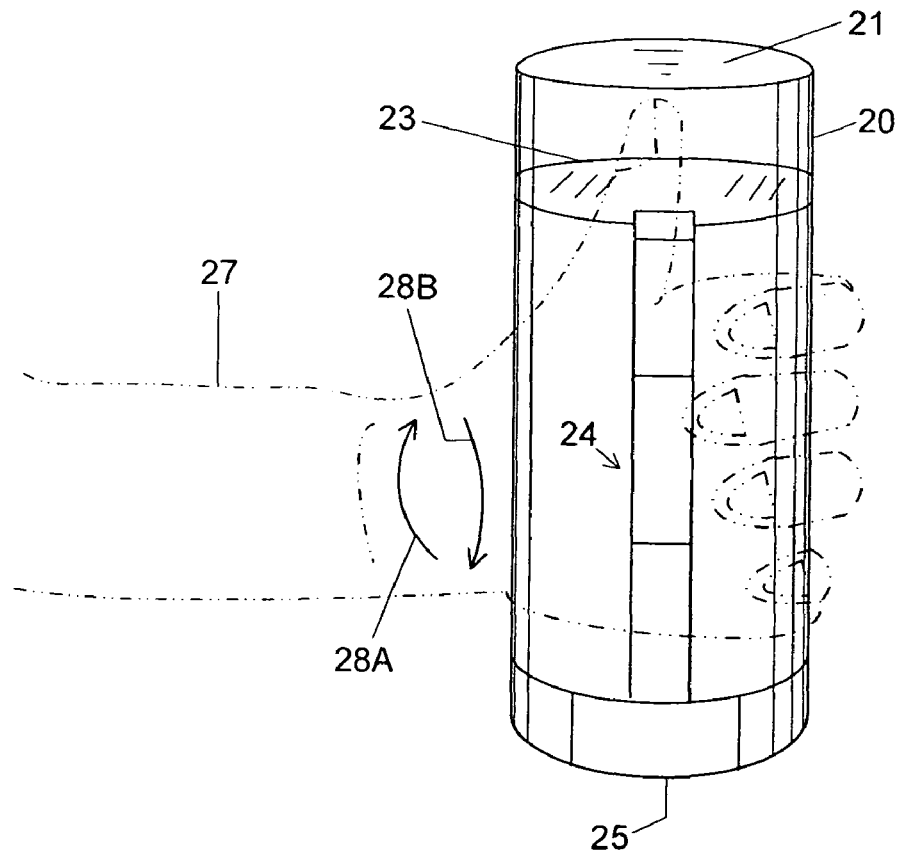
FIG. 5A shows a user side view with the subject's hand in a vertical start position.
Figure 5B:
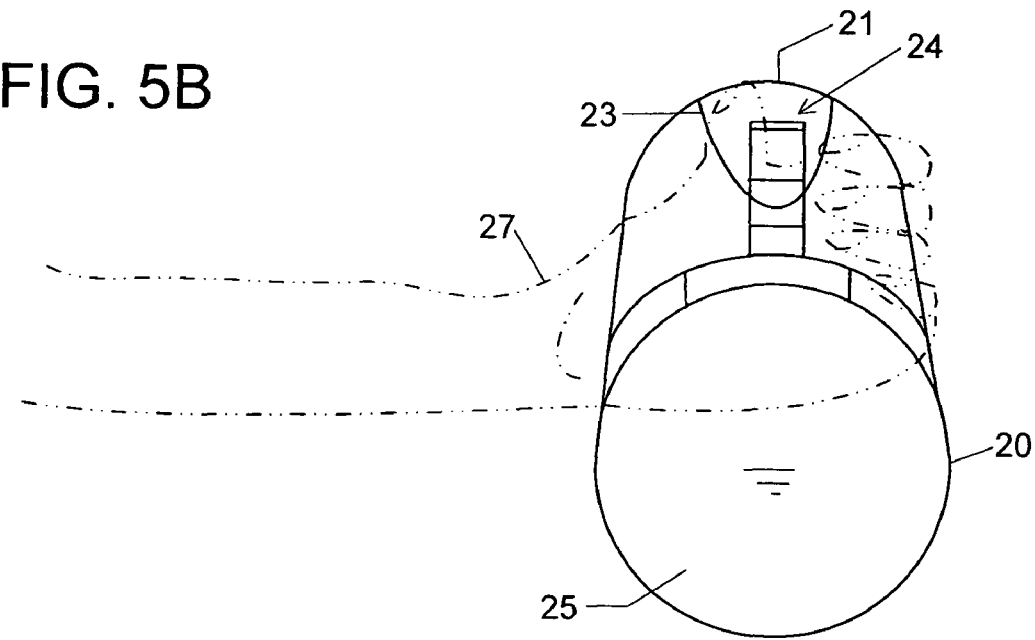
FIG. 5B shows a user side view with the subject's hand in a palm-up (supinated) posture.
Figure 5C:
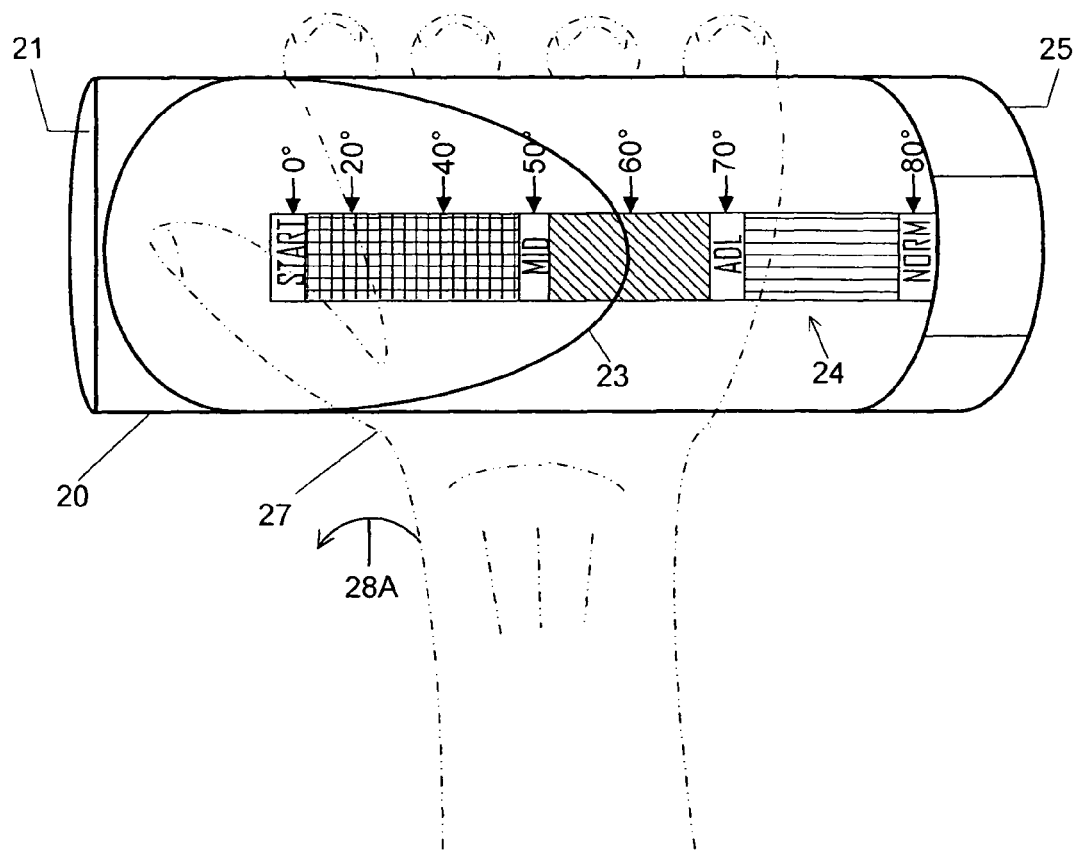
FIG. 5C shows a user top view with the subject's hand in a palm-up (supinated) posture.
Figure 5D:
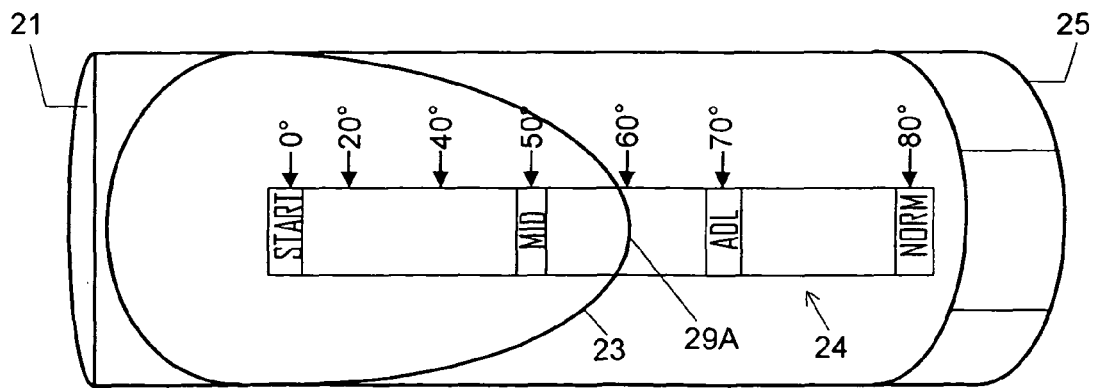
FIG. 5D shows a user top view of a palm-up (supinated) position, minus the user's hand.
Figure 6A:
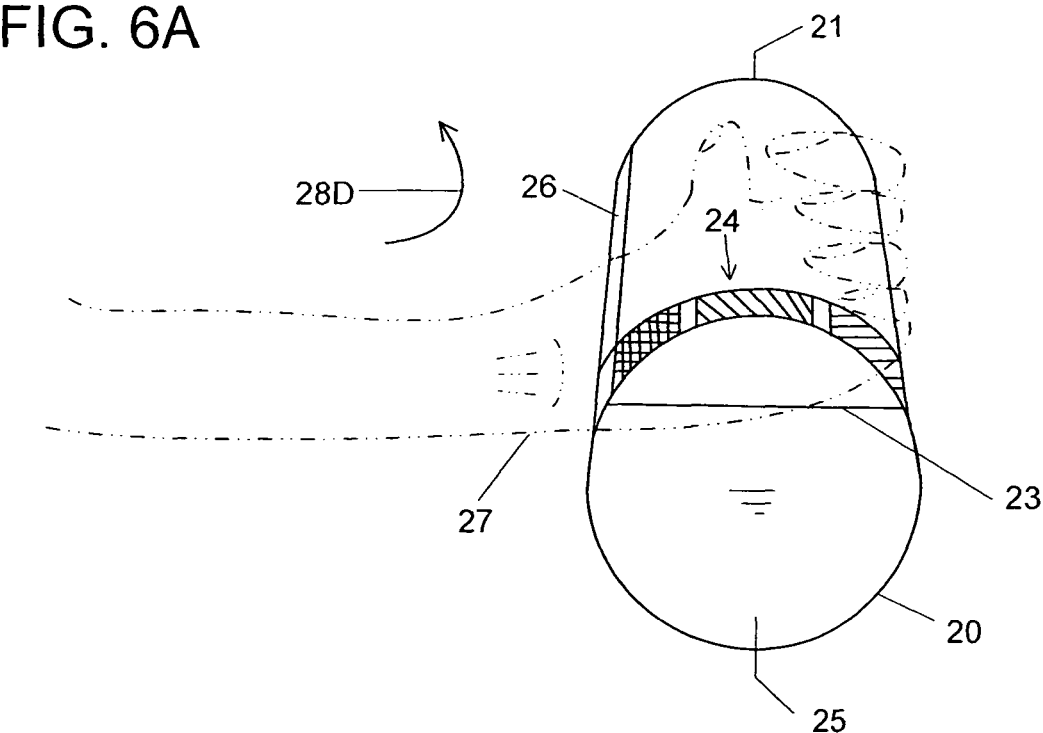
FIG. 6A shows a user side view with the subject's hand in a horizontal palm-up start position.
Figure 6B:
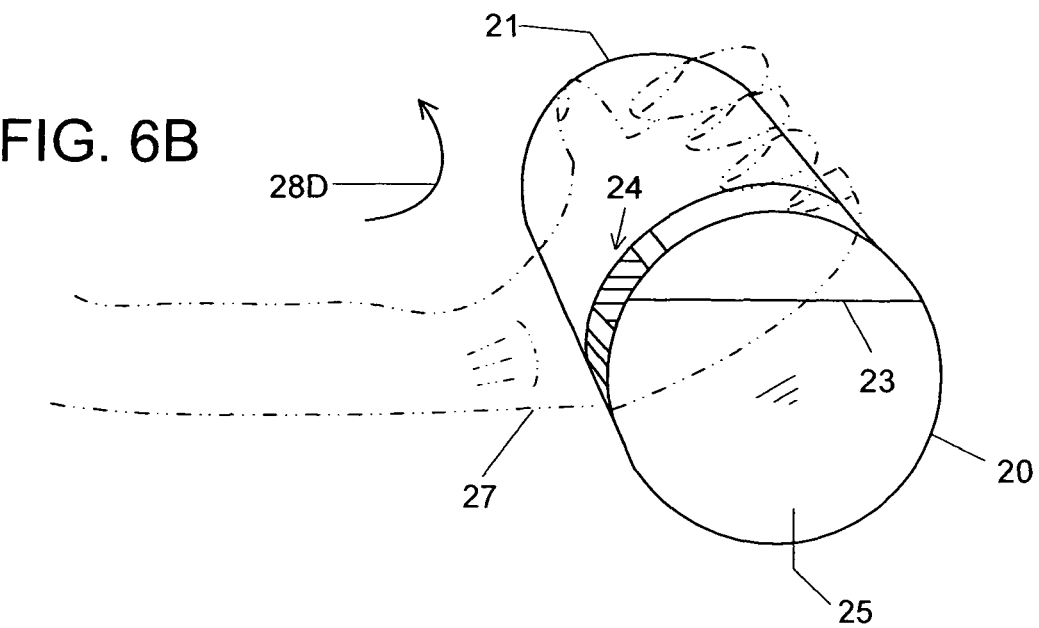
FIG. 6B shows a user side view with the subject's hand in a bent (flexed) posture.
Figure 6C:
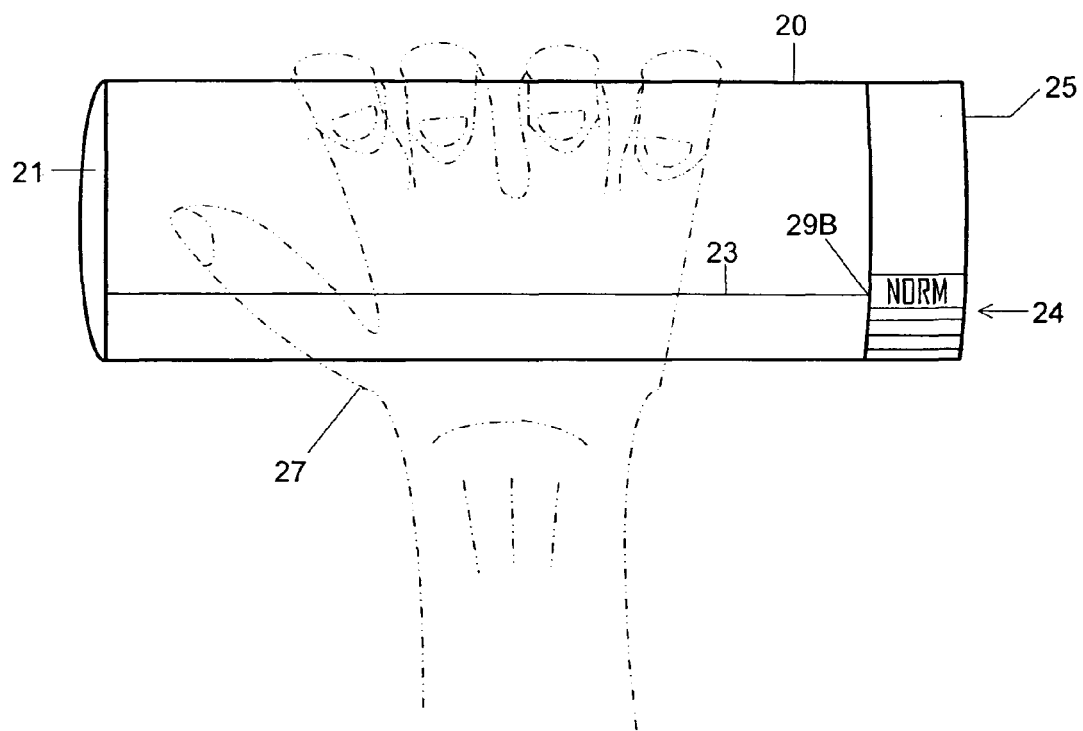
FIG. 6C shows a user top view with the subject's hand in a bent (flexed) posture.
Figure 7A:
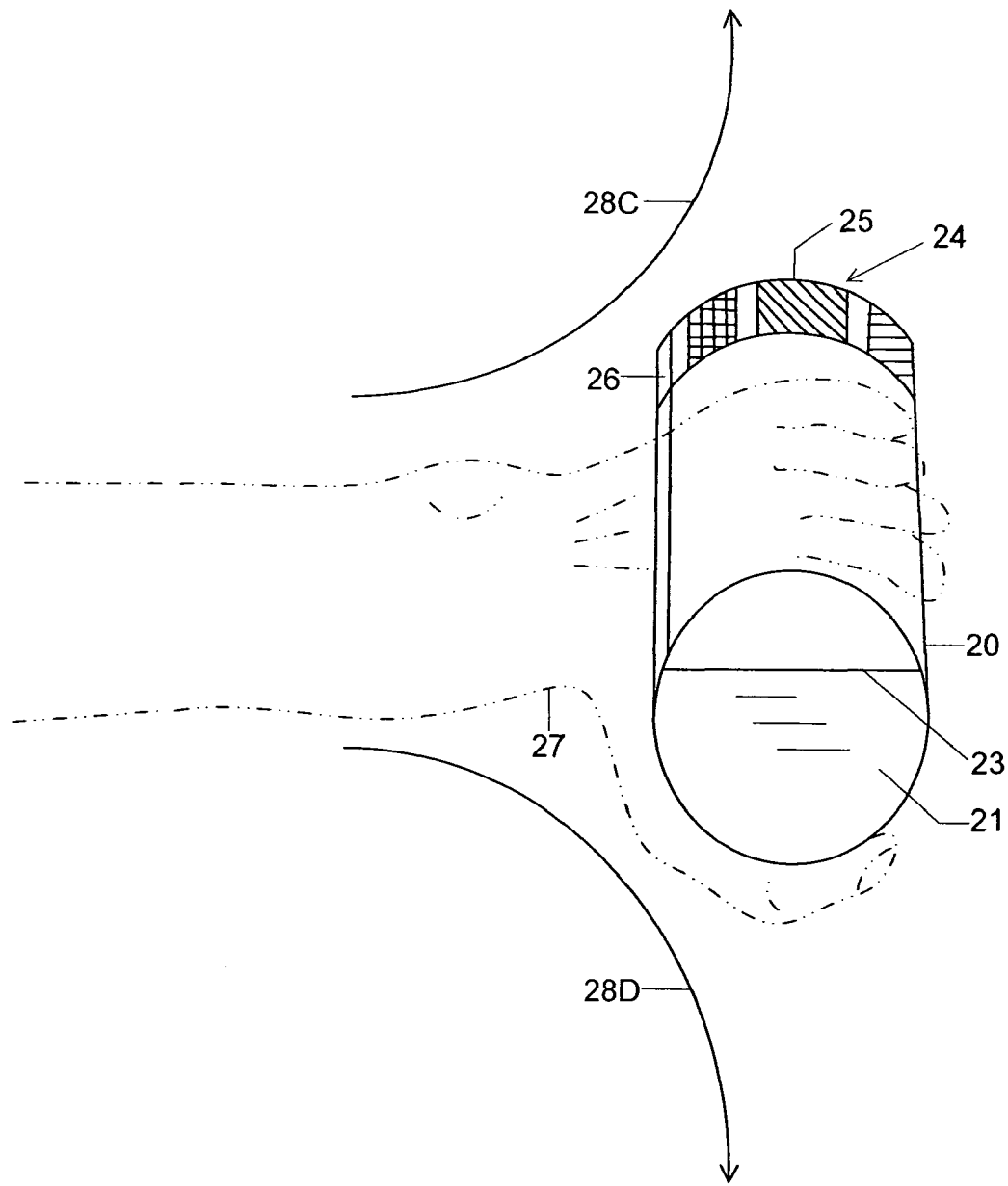
FIG. 7A shows a user side view with the subject's hand in a horizontal palm-down start position.
Figure 7B:
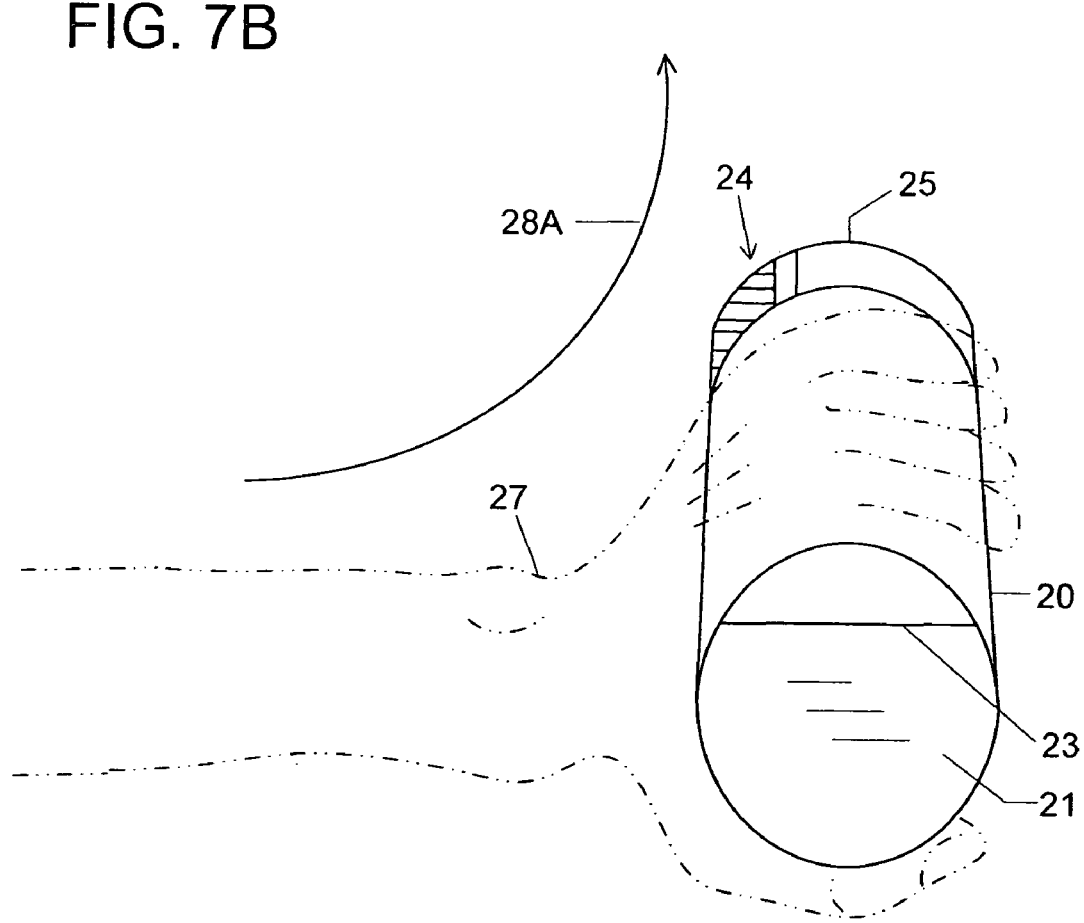
FIG. 7B shows a user side view with the subject's hand in an extension posture.
Figure 7C:
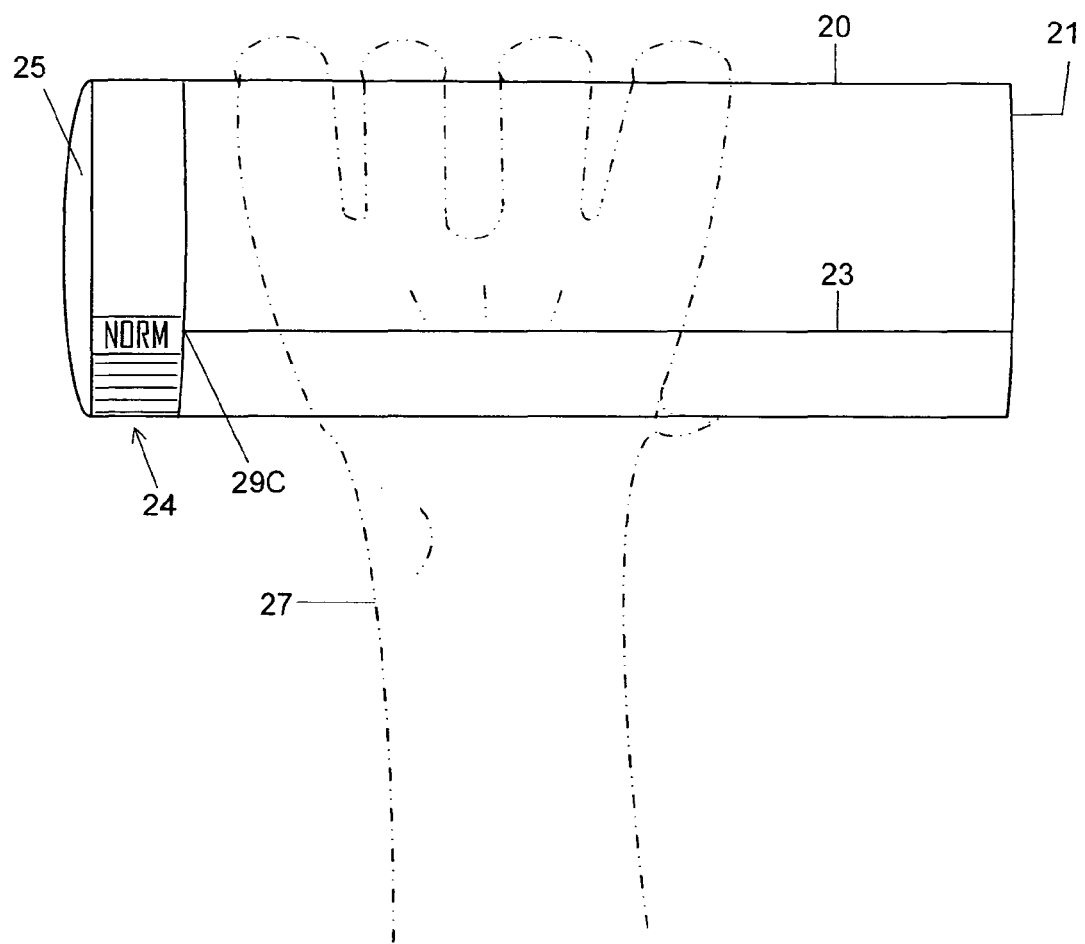
FIG. 7C shows a user top view with the subject's hand in an extension posture.

| DRAWINGS - REFERENCE NUMERALS | |
|---|---|
| 20 | Casing |
| 21 | Casing Top |
| 22 | Identification Area |
| 22A | Paper Label |
| 23 | Fluid |
| 24 | Calibration Scale Assembly |
| 24A | Measurement Marking |
| 24B | Subsection |
| 24C | Subsection Milestone |
| 25 | Casing bottom |
| 26 | Axis Marking |
| 27 | User Hand/Forearm |
| 28A | Supination Arrow |
| 28B | Pronation Arrow |
| 28C | Extension Arrow |
| 28D | Flexion Arrow |
| 28E | Ulnar Deviation Arrow |
| 28F | Radial Deviation Arrow |
| 29A | Measurement in FIG. 5D |
| 29B | Measurement in FIG. 6C |
| 29C | Measurement in FIG. 7C |
| 30L | Arrow for Lengthwise Shift |
| 30C | Arrow for Circumference Rotation |
| 31A | Full Sleeve |
| 31B | Partial Sleeve |
| 32 | Slot |
| 33A | Contour |
| 33B | Flat Surface |
| 34 | Handle |
| 35A | Casing opening protrusion |
| 35B | Casing opening |
| 35C | Casing opening cover |
| 36 | Top Protrusion |

GLOSSARY AND REFERENCE

1. The term "range of motion" means the arc of motion that occurs at a joint or series of joints.
2. The term "supinate" means to rotate or place the hand or forelimb so that the palmar surface is upward when the limb is stretched forward horizontally.
3. The term "pronate" means to rotate or place the hand or forelimb so that the palmar surface is downward when the limb is stretched forward horizontally.
4. The term "flexion" means bending, decreasing the angle between the bones of the limb at a joint (forward bending). This bending can occur in the palm up or palm down position.
5. The term "extension" means straightening out a flexed limb (backward bending).
6. The term "radial deviation" means movement towards the inside of the body when the limb is stretched forward horizontally (fingers towards the radius bone).

7. The term "ulnar deviation" means movement towards the outside of the body when the limb is stretched forward horizontally (fingers towards the ulna bone).
8. The term "sagittal plane" is the cardinal plane of the body that divides the body into left and right halves. Flexion and extension occur in this plane.
9. The term "frontal plane" is the cardinal plane of the body that divides the body into front and back halves. Pronation and supination occur in this plane when a person is in the starting position described in section B.2 of this application. When in the anatomical position, pronation and supination occur in the transverse plane. Radial and ulnar deviation also occur in the frontal plane.
10. The term "transverse plane" is the cardinal plane of body that divides the body into upper and lower halves.
11. Reference—Norkin, C and White, D: Measurement of Joint Motion—A Guide to Goniometery, ed 3. F A Davis, Philadelphia, 2003.

DETAILED DESCRIPTION

Figure 1:
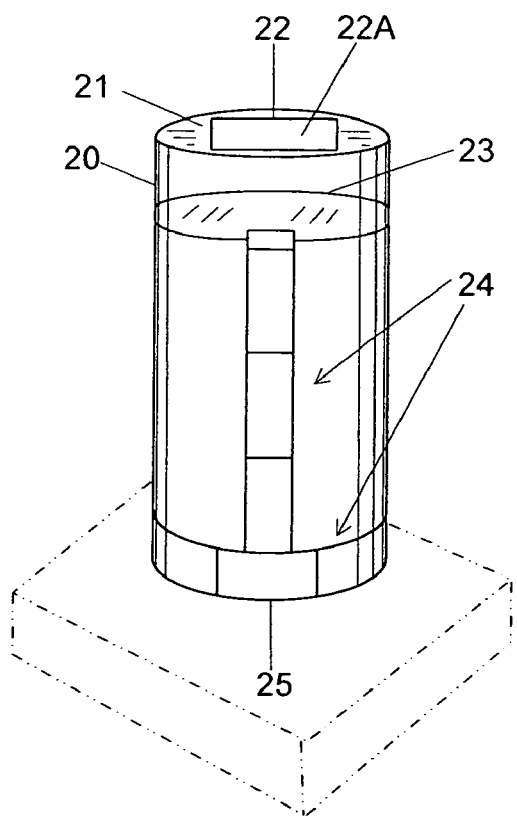
FIG. 1 is a front perspective view of one embodiment.
Figure 2A:
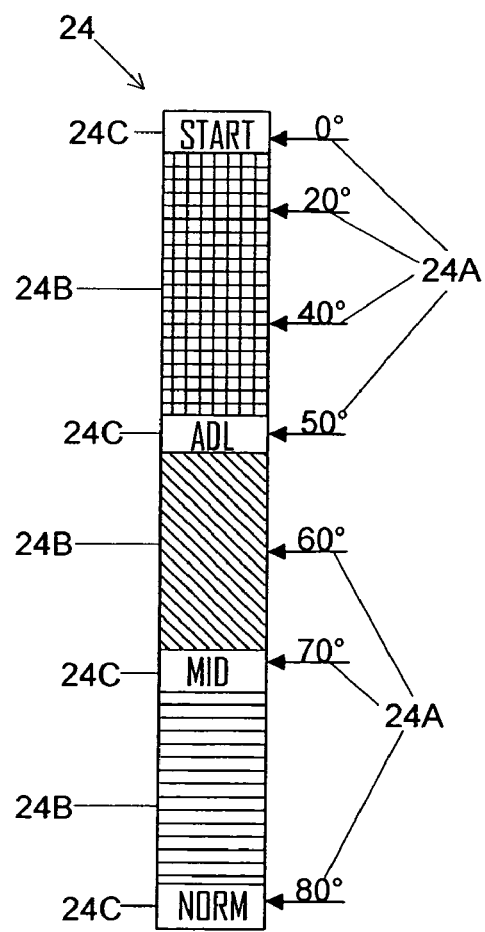
FIG. 2A is an enlargement of a calibration scale 24 assembly of one embodiment.
Figure 3:
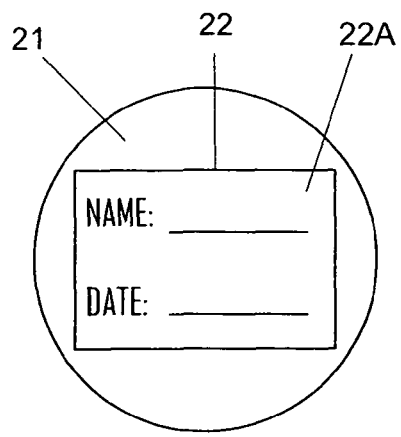
FIG. 3 is a view of the top of one embodiment.

One embodiment of the device is illustrated in FIG. 1 (front prospective view), FIG. 2A (exploded view), and FIG. 3 (top view). The device has a casing 20 of largely cylindrical shape primarily fabricated from substantially transparent colorless plastic, although other suitably water-tight and substantially transparent materials could be substituted. The material that casing 20 is fabricated from also has an exterior surface upon which a person can label or print, such that casing 20 can accommodate the addition of markings by the user, such as those made by a felt tip pen, dry erase marker, water-based pen, or the like (not shown).

The casing has an upper circular section (top) 21, a lower circular section (bottom) 25. Each is described below. The upper circular section (top) 21 and the lower circular section (bottom) 25 are referred to as top 21 and bottom 25 for the remainder of this application for ease of readability.

The top 21 of casing 20 contains an identification area 22 (FIG. 1 and FIG. 3), to provide a place where a person may write information. In the embodiment illustrated in FIG. 1 and FIG. 3, the identification area 22 includes a paper label 22A, which is adhesively attached to top 21 to provide a superior writing surface. In another embodiment, paper label 22A is omitted and the information is written directly on top 21 (not shown). In FIG. 3, identification area 22 is illustrated with a label for Name and Date for exemplary purposes.

The bottom 25 of casing 20 is a base member for supporting the device on a flat surface when not in use. In one embodiment, the circular edges of bottom 25 and top 21 are rounded to avoid snagging and personal injury (not shown).

The body of casing 20 is provided with a plurality of calibration scale 24 assemblies, which form bands of elements adhesively or fixedly attached to casing 20 (FIG. 1 and FIG. 2A). The calibration scale assemblies may be manufactured with conventional materials, such as, for example, plastic, paper, laminated paper, vinyl, cellulose acetate, polycarbonate resin thermoplastic, etc. The chosen material ideally is flexible, durable, has good draping and molding qualities, is colorfast to staining and persperation, impact resistant, and able to accept a coating of adhesive (if attached to casing 20 adhesively).

In the presently contemplated embodiment, the calibration scale 24 assemblies are configured to include narrow bands characterized by or arranged in a scale of degrees (FIG. 2A). However, other variations are possible, such as a different shape (e.g., an arrow) or a different size (e.g., wider) (not shown). The embodiment illustrated in FIG. 1 and FIG. 3 is configured to contain one or more calibration scale 24 assembly situated on the length of casing 20, and one or more calibration scale 24 assembly situated on the circumference of casing 20.

As illustrated in FIG. 2A (exploded view), a calibration scale 24 assembly includes:
a) A plurality of measurement markings 24A, to provide an incremental unit of measure for the calibration scale 24 (FIG. 2A). By way of example, the construction of measurement markings 24A illustrated in FIG. 2A is such that the unit of measure is in degree increments, each unit of measure is configured to have an arrow showing point on the calibration scale 24 assembly to which it applies.

Figure 2B:
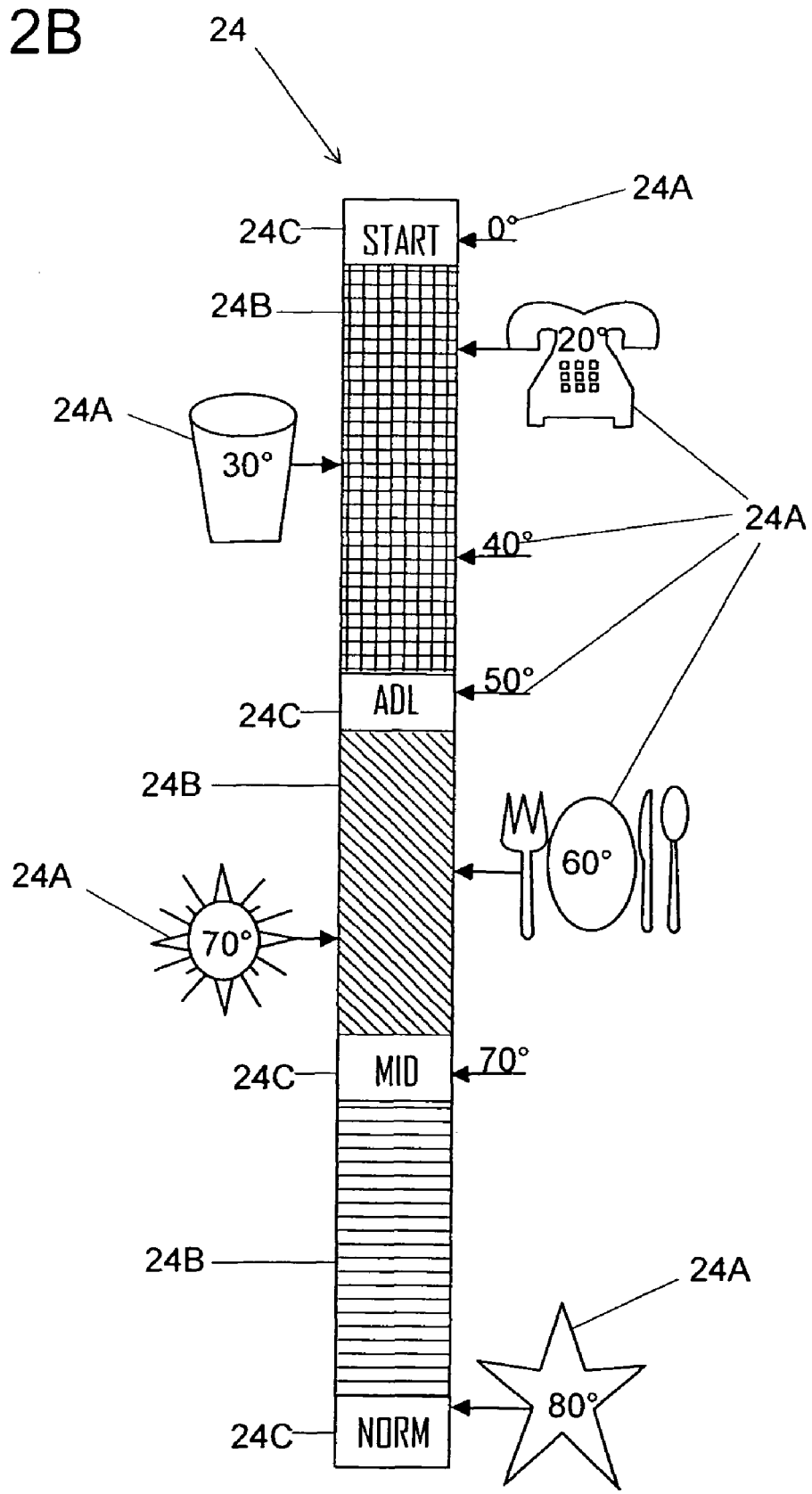
FIGS. 2B and 2C show an alternate version of the calibration scale 24 assembly.

Other variations are possible, as illustrated in FIG. 2B, where measurement markings 24A include graphical icons corresponding to a typical functional activity possible at a particular measurement. In FIG. 2B, which is an exemplary calibration scale 24 assembly for supination, a telephone graphical icon is aligned with a measurement marking 24A for 20°. This is consistent with research published in the book listed in the Glossary and Reference section of this application. The research indicates 20° of supination is required to use the telephone. In FIG. 2B, the calibration scale 24 assembly is shown enlarged for clarity.

The prototype of the device built for and by the inventor contains measurement markings made from labels printed using a home and office electronic label maker. The measurements were printed in black print on clear tape. The clear tape is durable, laminated, abrasion resistant, heat and cold resistant, UV resistant, and spill resistant.

b) A plurality of subsections 24B, to break the calibration scale 24 into segments (FIG. 2A). In the presently contemplated embodiment, subsections 24B are differentiated from each other by a plurality of colors. By way of example, the construction of the subsections 24B illustrated in FIG. 2A is such that each subsection is filled with a different color, such as red, yellow, green, and blue (these colors are exemplary). Other variations are possible: a subsection 24B can have one or more colors, or have a gradient of color such that the color increases in intensity throughout the subsection 24B (not shown).

The prototype of the device built for and by the inventor contains decorative artist's tape in red, yellow, green, and blue to provide the color for the adjacent subsections.

c) The subsections 24B are further defined by a plurality of subsection milestones 24C, to clearly differentiate the subsections from one another. In the embodiment illustrated in FIG. 2A, the exemplary milestones are configured to correspond with predetermined range of motion measurements as follows:
0° corresponds to the "START",
50° corresponds to "ADL", or Activities of Daily Living,
70° corresponds to "MID", or Mid range, and
80° corresponds to a "NORM".

This configuration aligns with research published in the reference indicated in the "Glossary and Reference" section of this patent application. In FIG. 2A, the subsection milestones 24C are configured to designate the following (for supination):
"START" designates the beginning of the calibration scale 24 assembly, "ADL" designates the point on the calibration scale 24 assembly corresponding to a measurement marking 24A where most Activities of Daily Living (ADL) are possible, "MID" designates the point on the calibration scale 24 assembly corresponding to a measurement marking 24A approaching the normal range, and "NORM" designates the point on the calibration scale 24 assembly corresponding to the mean value for supination.

Figure 2C:
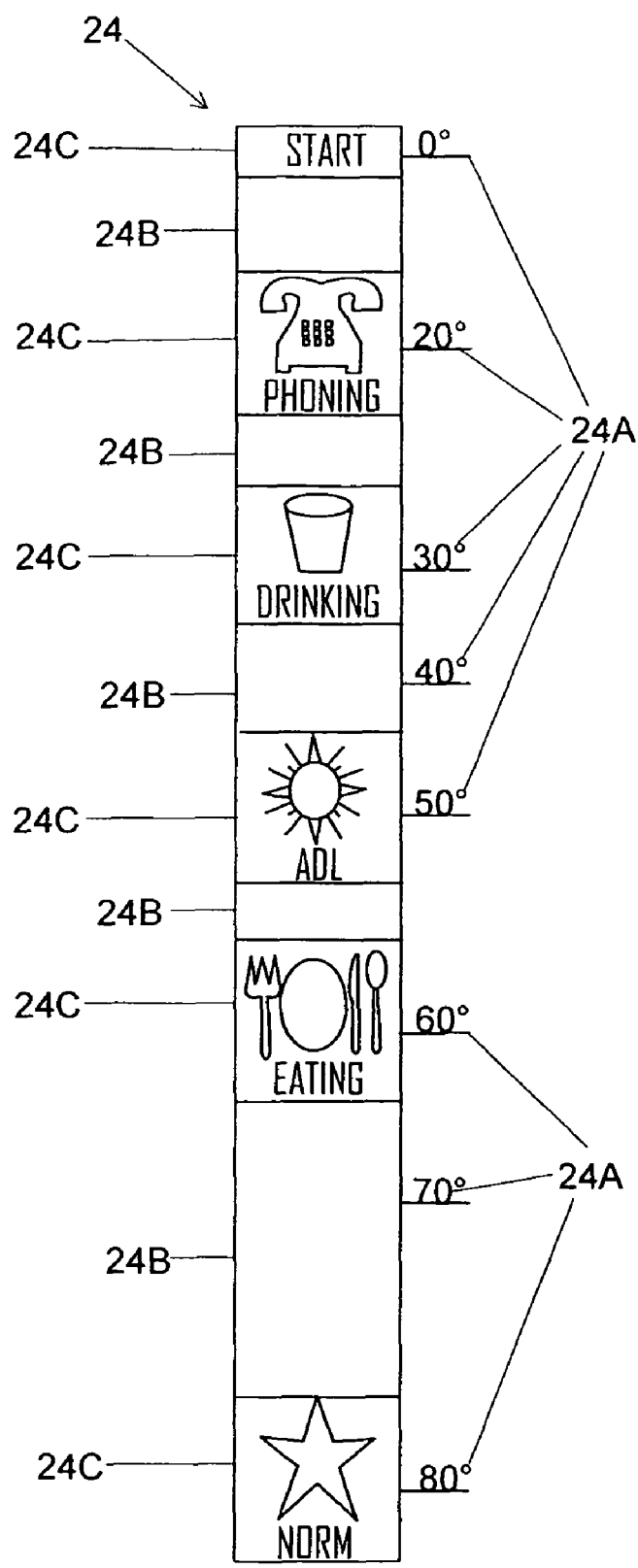

Other variations are possible, as illustrated in FIG. 2C, where subsection milestones 24C include a graphic icon for the functional activity corresponding to the range of motion on the scale. In FIG. 2C, which is an exemplary calibration scale 24 assembly for supination, a telephone graphical icon is configured as the subsection milestone 24C for 20° to create a milestone where a typical user has the range of motion required to use the telephone, and a fork and knife icon is located at 60° to create a milestone for feeding activities (FIG. 2C). Other similarly designed icons are also shown in FIG. 2C. In FIG. 2C, the calibration scale 24 assembly is shown enlarged for clarity.

Many drawing figures referred to in this application illustrate calibration scale 24 assembly without all of the elements shown in the exploded views in FIGS. 2A-2C for simplicity. An example is FIG. 5A, where a simplified calibration scale 24 assembly is shown.

Figure 4:
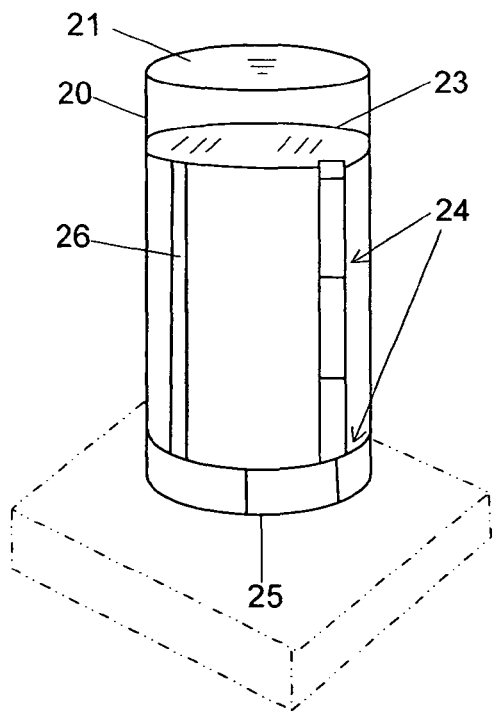
FIG. 4 is a side perspective view of one embodiment.

The body of casing 20 is further provided with axis markings 26, adhesively or fixedly attached to casing 20 and arranged to form either a line in a direction parallel with the length of casing 20 (FIG. 4), or the distance around casing 20 (not shown). In the presently contemplated embodiment, the axis markings appear in white, to differentiate them from other elements on the casing that may use color, such as subsections 24B.

A fluid 23 is contained within casing 20 (FIG. 1). In the presently contemplated embodiment, fluid 23 has a viscosity similar to water. However, fluids of other viscosities are possible. Fluid 23 is preferably clear and colorless, although it may be tinted or made opaque as desired.

Operation—FIGS. 5A-C, 6A-C, 7A-C, 8, 9, 12E, 14B

The following sections A, B, C, D, E, and F describe the operation of the embodiment. Some of the figures in this section provide a simplified view of calibration scale 24 assembly, rather than providing all the elements seen in the exploded view of the calibration scale 24 assembly illustrated in FIGS. 2A-C. This is done for simplicity purposes.

A. Introduction

This section describes the operation for four general uses of the device.

First, sections B-C below describe how to operate the device for range of motion measurement.

Second, section D below describes how to operate the device for stretching.

Third, section E below describes how to operate the device for exercise.

Finally, section F below describes how to operate the device for benchmarking and motivation.

For each use, the device is suitable for use in either the left or the right hand. It also finds uses when used by one hand, while the other hand assists. Other uses are possible, the usage of the device is not limited to these four general ways.

B. Range of Motion Measurement

Overview

B.1 General Overview

The manner of using the device to measure wrist and forearm joint motion is similar to that of performing common therapeutic exercises designed for a patient's home-based rehabilitative regimen. This ensures that the device is both easy to use and well suited for patient use. For example, one common exercise involves turning one's palm upward and holding it in that position for 5 seconds. This exercise helps the patient gain back the range of motion necessary to achieve the palm up (supination) position. Continuing with this example, operating the device to measure the range of motion for supination involves performing that same motion (turning ones palm up) while holding the device with chosen hand. Thus, since the motions involved in using the device mimics the rehabilitative exercises the person is likely already familiar with, it is very intuitive to use.

The range of motion measurement is accomplished due to the reaction of fluid 23 to the downward pull of gravity. Specifically, the fluid moves inside the casing when a user holding casing 20 performs various pre-determined movements. As fluid 23 changes positions inside of casing 20, the user views the appropriate calibration scale 24 for the movement performed. It is the location of fluid 23 on calibration scale 24 that provides a visual indicator of the range of motion.

An elegant and user-friendly feature of the embodiment is its suitability to assess multiple measurements (e.g., supination, flexion, extension, etc.) of range of motion simply by gripping the device, performing movements, and observing the location of the fluid on the calibration scale 24 assembly. The details are provided in section C.

Further, having one or more calibration scale 24 assembly on the length and circumference of casing 20, by selecting the appropriate scale to use, a user can measure movements in more than one of the cardinal planes (i.e., sagittal, frontal, and transverse) of the body. Refer to the Glossary and Reference section of this application for high-level definitions.

In addition, the embodiment is suitable for measuring both active and passive range of motion. For active range of motion, the user moves the joint exclusively with the muscles in that joint. For passive range of motion, the user can use his or her other hand to assist, or another person can help move the joint. Regardless of the method, the range of motion measurement is obtained by the location of fluid 23 on the appropriate calibration scale 24 assembly.

B.2 Position Overview

The user gets into the starting position by bending the elbow of the chosen arm to 90°. The upper arm is kept close to the body to stabilize the user and isolate desired motion. Next, the user grasps casing 20 in the chosen hand 27, as illustrated in FIG. 5A. In the illustration, the user's left hand is gripping casing 20 such that his or her palm and fingers are wrapped around casing 20, with his or her thumb pointing straight up. An alternative grip includes wrapping the user's thumb around the front of casing, as one might grip a glass to drink from it (not shown). In this position, the user is ready to use the device to perform various movements and obtain a measurement of range of motion. The user may sit in a chair throughout this process if he or she finds it more comfortable.

B.3 Overview of Selected Movements

A brief description of selected measurements (including supination, flexion, extension, pronation, radial deviation and ulnar deviation) is below. After this brief description, details are provided in section C below.

For a measurement of supination, casing 20 is held in the starting position shown in FIG. 5A (the left hand is shown in FIGS. 5A-5C) and moved in the direction of arrow 28A, to the palm up position. FIG. 5B illustrates the end position after the movement for a patient that can achieve the full palm up (supinated) position. A calibration scale 24 situated on all or part of the length of casing 20 provides the range of motion measurement (FIG. 5C). Further details are provided in section C.1.

For a measurement of flexion, casing 20 is held in the starting position shown in FIG. 6A (the left hand is shown in FIGS. 6A-6C) and moved in the direction of arrow 28D. FIG. 6B illustrates an exemplary end position after the movement is performed. A calibration scale 24 assembly situated on all or part of the circumference of casing 20 provides the range of motion measurement (FIG. 6C). This is very similar to how supination was measured, with the exception that with supination, the calibration scale 24 assembly used is arranged lengthwise on casing 20, and for flexion, the calibration scale 24 assembly used is arranged around the circumference of casing 20. Further details are provided in section C.2. In addition, an alternative method for flexion is provided in section C.3.

For a measurement of extension, casing 20 is held in the starting position shown in FIG. 7A (the left hand is shown in FIGS. 7A-7C) and moved in the direction of arrow 28C for extension. A calibration scale 24 assembly situated on all or part of the circumference of casing 20 provides the range of motion measurement. Further details are provided in section C.4.

For a measurement of pronation, casing 20 is held in the starting position shown in FIG. 5A (the left hand is shown) and moved in the direction of arrow 28B, to the palm down position. A calibration scale 24 situated on all or part of the length of casing 20 provides the range of motion measurement. Further details are provided in section C.5.

Figure 8:
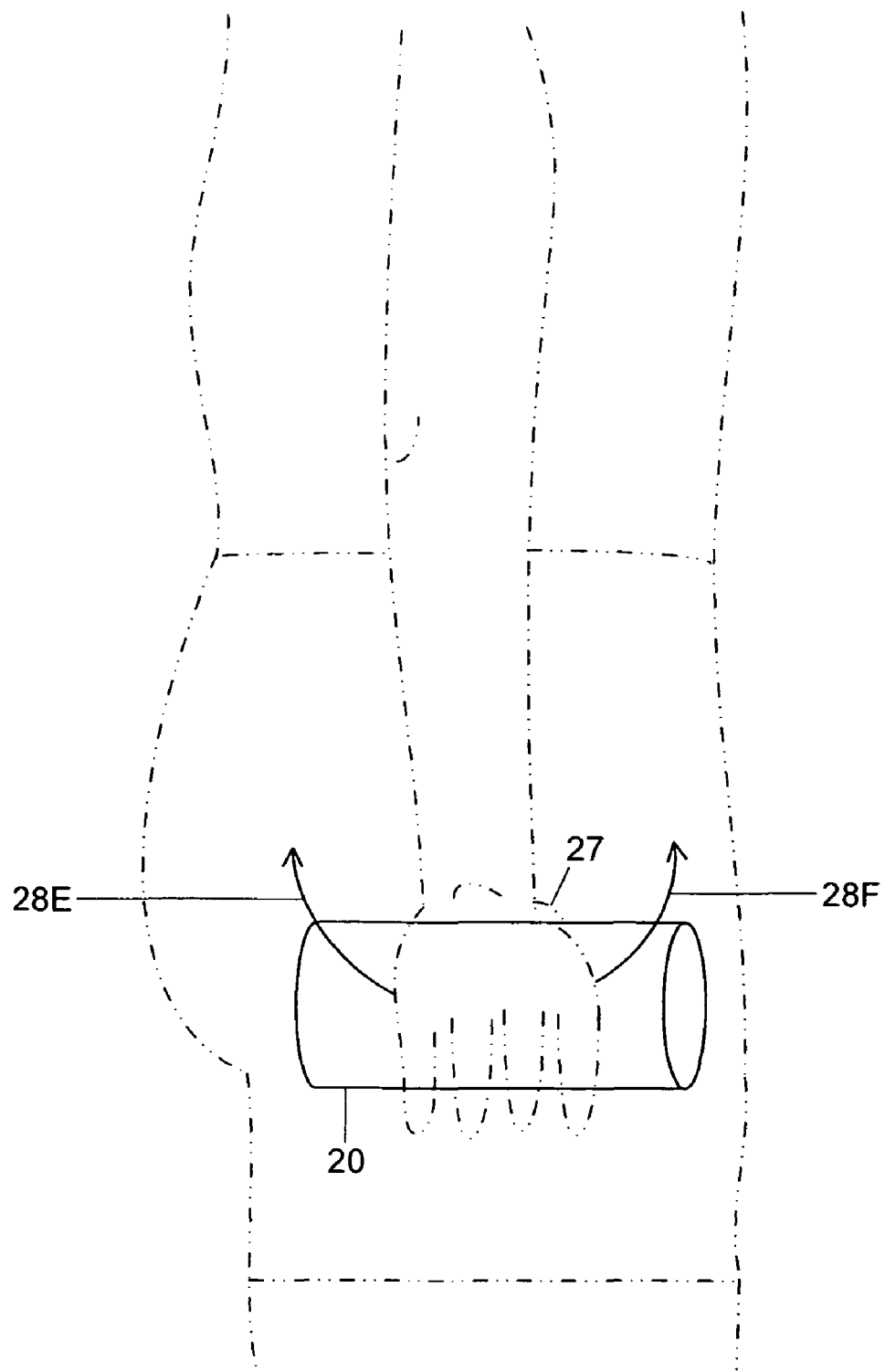
FIG. 8 shows a side prospective view with the subject's hand in a straight-arm start position.

For a measurement of radial deviation and ulnar deviation, casing 20 is held in the starting position shown in FIG. 8 (the right hand is shown in FIG. 8) and moved in the direction of arrow 28E for ulnar deviation or arrow 28F for radial deviation. A calibration scale 24 assembly situated on all or part of the length of casing 20 provides the measurement. Further details are provided in section C.6.

C. Range of Motion Measurements

Details

C.1 Supination (FIGS. 5A-5C Show the Left Hand, 5D Removes the Hand)

For a measurement of supination, casing 20 is held in the starting position illustrated in FIG. 5A. In this position, top 21 is pointed up, and bottom 25 is pointed towards the floor. Then, the user rotates his or her forearm in the direction of arrow 28A (counter clock-wise from the user's perspective for the left hand). This rotation brings the hand into a palm-up posture (FIG. 5B). It also brings top 21 to point in a direction towards the outside of the body, and bottom 25 to point in a direction across the inside of the body (FIG. 5B).

As the user rotates his or her forearm, gravitational force keeps fluid 23 coplaner with the ground, which causes fluid 23 to move along a calibration scale 24 assembly, situated lengthwise on casing 20. This fluid movement is evident by comparing the position of fluid 23 in the start position (FIG. 5A), with the position of fluid 23 in the supinated (palm up) position (FIG. 5B). In the start position, fluid 23 is in largely circular shape. In the supinated (palm up) position, it is in an arch shape with the mid-point pointing to the position on calibration scale 24 assembly corresponding to the measurement of range of motion.

When the user has rotated his or her forearm until resistance is felt and no additional movement is possible, he or she obtains the range of motion measurement by viewing the ending position of fluid 23 on calibration scale 24 assembly as a visual indicator of the measurement (FIG. 5C). In FIG. 5C, this measurement is aligned with the portion of calibration scale 24 assembly denoted by a green color. The colors shown in FIG. 5C are not shown in FIG. 5A, 5B, or 5D for simplicity. The measurement is pointed out in FIG. 5D by reference numeral 29A. FIG. 5D is similar to FIG. 5C with certain elements removed for clarity.

C.2 Flexion—Palm Up (FIGS. 6A, 6B, and 6C Show the Left Hand)

An elegant feature of the embodiment is that it empowers the user to obtain a measurement of flexion, in a manner that flows easily from the measurement of supination described in section C.1 above. The ending position of supination leaves the user in the palm up posture. From here, for a measurement of flexion the user simply repositions casing 20 in his or her hand to align fluid 23 to axis marking 26 (FIG. 6A). Then, the user bends (i.e., curls) his or her wrist in the direction of arrow 28D illustrated in FIG. 6A. This bending movement curls the user's fingers in a direction that brings them closer to the upper body (FIG. 6B). This motion is similar in form to a biceps curl, except that instead of the bending occurring at the elbow, the bending occurs at the wrist.

As the user bends his or her wrist, gravitational force keeps fluid 23 coplaner with the ground, which causes fluid 23 to move along a calibration scale 24 assembly situated around a portion of the circumference of casing 20. This fluid movement is evident by comparing the position of fluid 23 in the start position (FIG. 6A), with the position of fluid 23 in the bent (flexed) position (FIG. 6B). In both FIGS. 8 and 9, fluid 23 is coplaner with the floor. However, in FIG. 6A, fluid 23 is aligned with axis marking 26, and in FIG. 6B, fluid 23 is aligned with the portion of the calibration scale 24 assembly that is denoted by a blue color. In FIG. 6B, axis marking 26 is not visible since it is now out of sight due to the curling movement.

When the user has bent (flexed) his or her wrist up until resistance is felt and no additional movement is possible, he or she obtains the range of motion measurement by viewing the ending position of fluid 23 on calibration scale 24 as a visual indicator of the measurement (FIG. 6C). This ending position is pointed out in FIG. 6C by reference numeral 29B, which is aligned with a subsection milestone 24C that is labeled to read 'NORM'.

C.3 Flexion—Palm Down (FIG. 7A Shows the Left Hand)

Consistent with the embodiment's elegant feature that enables the user to easily move from the supination measurement described in C.1 to the flexion measurement described in C.2, the device empowers the user to obtain an alternate measurement of flexion in a manner that also flows easily from earlier movements. From the ending position of the first alternative for flexion (described in C.2) the user simply rotates his or her forearm to reach the palm down position (FIG. 7A). From here, for a measurement of flexion in the palm down posture, the user simply repositions casing 20 in his or her hand as necessary to align fluid 23 to axis marking 26 (FIG. 7A). Then, the user bends (i.e., curls) his or her wrist down in the direction of arrow 28D (FIG. 7A). This bending movement curls the user's fingers in a direction that brings them closer to the lower body (not shown).

From here, the operation is similar to flexion in the palm up posture (described in section C.2). When the user has bent his or her wrist down until resistance is felt and no additional movement is possible, he or she obtains the range of motion measurement by viewing the ending position of fluid 23 on calibration scale 24 assembly as a visual indicator of the measurement (not shown). Due to the similarities to flexion in the palm up position, the details are not repeated here for brevity.

C.4 Extension (FIGS. 7A, 7B, and 7C Show the Left Hand)

Similarly, the embodiment's design empowers the user to obtain a measurement of extension (also known as a reverse curl), in a manner that flows easily from the measurements described in sections C.1-C.3 above. The user keeps his or her hand the palm down position from the flexion measurement described in section C.3. From here, for a measurement of extension, the user ensures fluid 23 is aligned to axis marking 26 (FIG. 7A). Then, the user bends his or her wrist up in the direction of arrow 28C illustrated in FIG. 7A. This upwards bending movement brings the back of the user's hand closer to the top of his or her forearm (FIG. 7B).

As the user bends his or her wrist up, gravitational force causes fluid 23 to move along a calibration scale 24, assembly situated around a portion of the circumference of casing 20. The fluid's movement is evident by comparing the position of fluid 23 in the start position (FIG. 7A), with the position of fluid 23 in the bent up (extension) position (FIG. 7B). In FIG. 7A, fluid 23 is aligned with axis marking 26, and in FIG. 7B, fluid 23 is aligned with the portion of calibration scale 24 that is denoted by a blue color. In FIG. 7B, axis marking 26 is not visible since it is now out of sight due to the bending up movement.

When the user has bent his or her wrist up until resistance is felt and no additional movement is possible, he or she obtains the range of motion measurement by viewing the ending position of fluid 23 on calibration scale 24 assembly as a visual indicator of the measurement (FIG. 7C). This ending position is pointed out in FIG. 7C by reference numeral 29C, which is aligned with a subsection milestone 24C that is labeled to read 'NORM'.

C.5 Pronation (FIG. 5A Shows the Left Hand)

For a measurement of pronation, the user positions the casing 20 such that it is in the starting position illustrated in FIG. 5A, and rotates his or her wrist to the palm down position in the direction of arrow 28B (such that the palm is facing the floor) until resistance is felt and no additional movement is possible. At this point, the user obtains the measurement by viewing the ending position of the fluid 23 on calibration scale 24 as a visual indicator of the measurement. Other options for measuring pronation are described in the operation sections for other embodiments.

C.6 Radial and Ulnar Deviation (FIG. 8 Shows the Right Hand)

To obtain a measurement of radial and ulnar deviation, the user gets into the starting position illustrated in FIG. 8, where the chosen arm is straight by the user's side (the right side arm is shown as an example in FIG. 8). While keeping his or her arm at rest, the user bends his or her wrist in direction of arrow 28F (towards the front of the body and the radius bone) for radial deviation. For ulnar deviation, the user bends his or her wrist in the direction of arrow 28E (towards the back of the body and the ulna bone).

From here, the operation is similar to all of the other range of motion measurements described in sections C.1-C.5 above. When the user has bent his or her wrist in the desired direction until resistance is felt and no additional movement is possible, he or she obtains the range of motion measurement by viewing the ending position of fluid 23 on calibration scale 24 assembly as a visual indicator of the measurement (not shown). Due to the similarities of this operation to the other positions, the details are not repeated here for brevity.

D. Stretching

Figure 9:
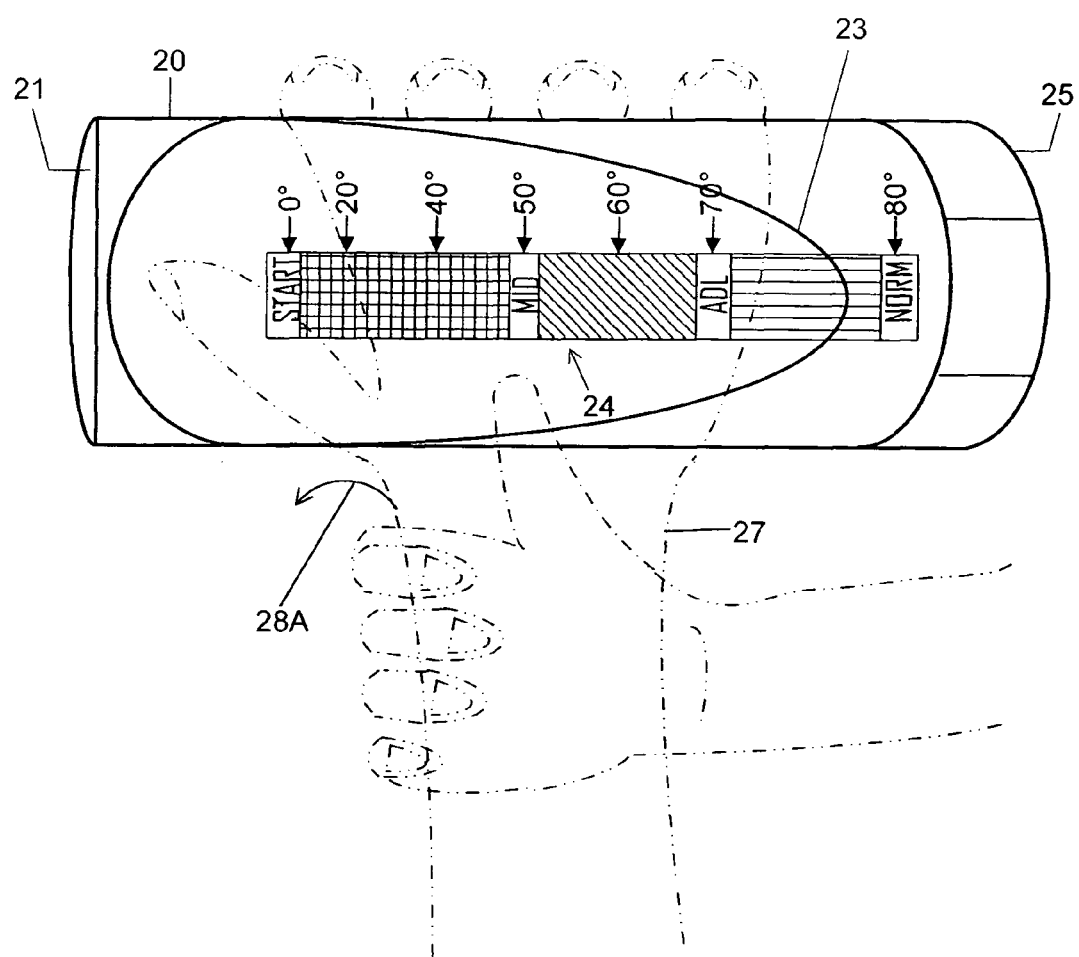
FIG. 9 shows a user top view where two hands are used.

The device is suitable for use by people who perform stretches to return mobility to their wrist and forearm. To use the device for stretching, the user completes the same motions described in section C above, continuing the active range of motion until resistance is felt. Then, the user makes use of his or her other hand, to gently stretch and increase the range of motion. For example, one common stretch for supination involves turning one's palm upward and then grasping it with the other hand and slowly turning it to the palm up position. Operating the device for a stretch involves performing that same motion, while holding the device in the hand. An example for supination is shown in FIG. 9, where the user's second hand (right) assists the left hand, which is holding casing 20. The user completes the stretch by continuing the rotation in the direction of arrow 28A, which is further into the palm up (supination) posture using both hands.

In addition to using the device for stretching by completing the motions described in section C, the user may use it for other rehabilitative stretches assigned by a medical practitioner.

The inventor of this device effectively used this stretching operation using a self-made prototype of the device. An elegant feature of this stretching operation is the location of fluid 23 on calibration scale 24 assembly as the stretch is performed, which provides instant knowledge of whether or not the stretch is deepening. It empowers the user with the ability to assess how far the stretch is achieved each time. This is helpful for both motivation and communicating progress to a medical practitioner. Furthermore, when the device is held such that its length is parallel to the floor (e.g., FIG. 7A), fluid 23 provides a visual indicator of whether or not casing 20 is held level by the user. The inventor has personal experience that dictates this is valuable information on the user's form.

E. Exercise

To use the device for exercise, the user completes the same motions as described in section C above, continuing to perform the exercises for a defined number of repetitions (e.g., 15-20). For example, one common exercise for supination and pronation involves turning one's palm upwards and downwards. Operating the device for exercise involves performing that some motion, while gripping the device. When performing the repetitions of the motions, the device acts as resistance by virtue of its own weight.

An example is shown in FIG. 7A, where the exercise is completed by moving in the direction of arrows 28C and 28D for the desired number of repetitions. Further, the location of fluid 23 within casing 20 provides useful visual guidance for the user to verify his or her form. For example, the user can confirm that the device is being held level throughout the exercise if the fluid remains level as the motion is performed.

In addition to using the device for exercise by completing the motions described in section C above, the user may use it for other rehabilitative exercises assigned by a medical practitioner.

F. Benchmarking and Motivation

There are two general ways the device may be used for benchmarking.

F.1 Establishing a Norm

In this case, the patient's healthy limb is used to establish a norm for comparing with the affected side, provided the healthy limb is not impaired or used selectively in athletic or occupational activities. Once obtained, this norm is compared with the range of motion of the impaired joint. To employ the device to establish a norm, the user may use a felt tip pen, dry erase marker, water-based pen, or other writing implement to hand-write a mark on casing 20 denoting the location of the benchmark. This is possible due to an embodiment having a surface upon which the user can label or print. This way, whenever he or she uses it, the mark serves as a visual guide and reminder of the norm, which has a motivating influence to improve the impaired side.

F.2 Recording Milestones and Progress

As the device user's impaired joint improves, he or she may write on casing 20, to mark milestones, progress, and improvements. When this information is written along side of calibration scale 24 assembly, it helps the user relocate previously attained measurement points. This provides the user with a visual means of progress, which can validate that the user is benefiting from the home-based therapeutic program. This is especially evident in an embodiment of the device where calibration scale 24 assembly is configured to employ color in adjacent subsections 24B (FIG. 2). Using color as a memory aid, users can easily remember if they are in the green zone or the blue zone, for example.

The inventor of the device successfully employed the device in this way, and found it extremely beneficial in her recovery from a broken wrist. An example outside of the realm of this device where milestones are used is that of touching ones toes. It is something to reach for, and once attained, it is a milestone a person can use to ensure he or she is not losing flexibility. Back to the realm of this device, operating the embodiment as described in this section is particularly useful for identifying increases, decreases, and plateaus for joint range of motion.

This completes sections A-F. Additional embodiments are described below.

Figure 10:
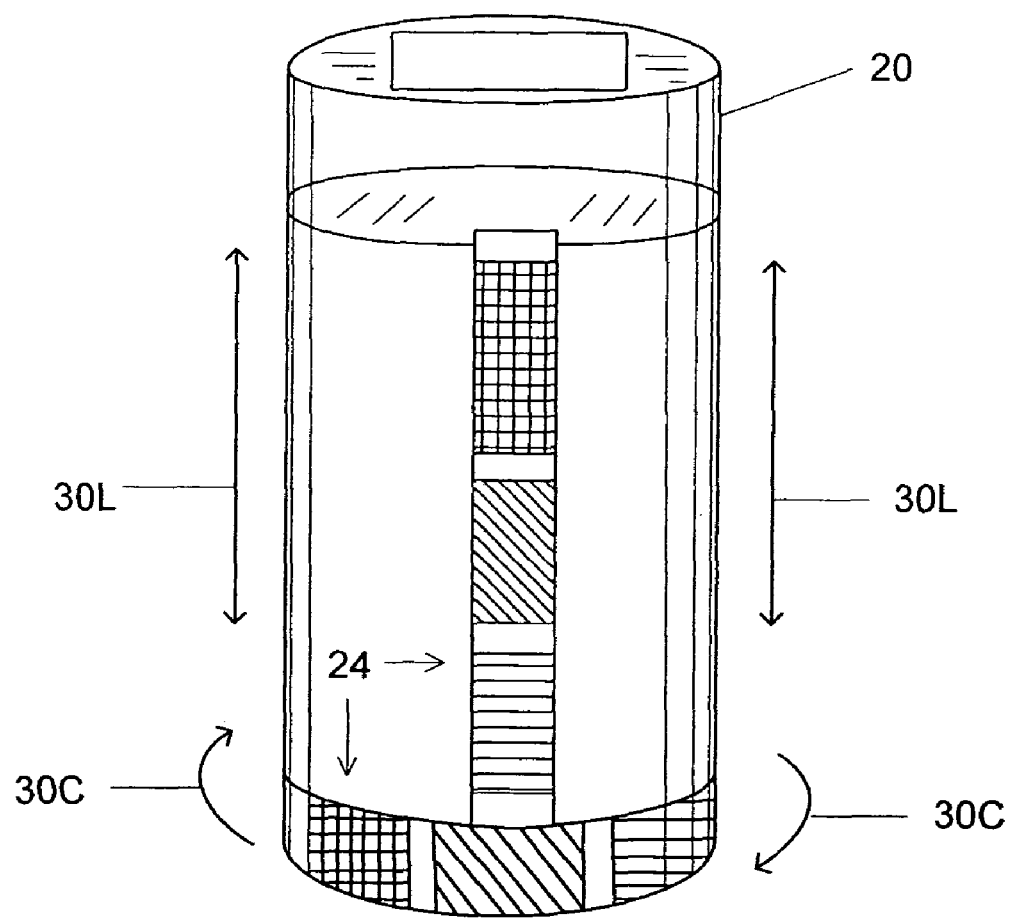
FIG. 10 shows a front perspective view of another embodiment.

FIG. 10—Description—Additional Embodiment—Adjustable Version

In FIG. 10, the calibration scale 24 assembly is adjustably attached to casing 20, which is formed of a material with a slide-able surface. Arrows 30L and 30C illustrate the adjustability directions for the calibration scales 24 assemblies.

The inventor presently contemplates two variations for securing the calibration scales 24 once adjusted by a user. In one variation of this embodiment, casing 20 is configured to contain multiple pre-determined locations along casing 20 into which the user can re-locate calibration scale 24 (not shown). In this variation, the adjustable elements are secured within the pre-determined location by a groove (not shown). Another variation of this embodiment is configured such that a user is able to re-locate calibration scale 24 to nearly any location along casing 20 (not shown). In this variation, casing 20 and calibration scale 24 are eccentric, each having a slightly different circumference. The eccentricity is configured in such a manner to secure the adjustable elements snugly in the desired location. However, other configurations for securing the adjustable items are possible, such as using adhesive or a notch attached to the casing that firmly yet releasably secures the items (not shown).

Operation—Additional Embodiment—Adjustable Version

The use of the embodiment is largely similar the operation described in the above operation sections A-F When operating this embodiment, the user adjusts calibration scale 24 to the desired location. This includes sliding movements along the embodiment's length, and rotation around its diameter. This adjustment enables the user to control the location of the measurement area and to zero the embodiment as necessary. It also enables users of varying capabilities to adjust the device to suit their individual needs. Once calibration scale 24 is in the desired location, the user secures it in place to prevent further movement when the embodiment is in use.

FIGS. 11A and 11B—Description Additional Embodiment—Releasable Version

In FIGS. 11A and 11B, the calibration scale 24 assembly is releasably attached to casing 20, which is formed of a material with a slide-able surface. In FIG. 11A, a sleeve 31A, formed of a thin pliable material, is configured to fit on casing 20. The inventor presently contemplates two variations for securing the calibration scale 24 assembly once put into place by the user. In one variation, casing 20 is configured to contain a slot 32, to support the addition, removal, adjustment, and securing of the releasable calibration scale 24 assembly (FIG. 11A). Another variation of this embodiment is configured to contain a plurality of notches or a continuous groove on the casing to secure the releasable items in place (not shown). However, other variations are possible, including using an adhesive, lip, groove, or housing to secure the releasable elements.

FIG. 11B illustrates a different version of this embodiment, similar in sprit with the version illustrated in FIG. 11A, however in this version sleeve 31B is in two separate pieces, whereas in FIG. 11A, sleeve 31A is one piece. Other design elements are similar between the two versions (FIGS. 11A and 11B). Slot 32 does not appear in FIG. 11B to illustrate a version of the embodiment that does not contain it.

Operation—Additional Embodiment—Releasable Version

The use of the embodiment is largely similar to the operation described in the above operation section A-F. When operating this embodiment, the user selects one or more calibration scale 24 assembly to use, and inserts the selection into slot 32 (FIG. 11A), or uses other securing elements configured on the device (not shown). When the user is finished using the embodiment, he or she may remove the selected elements, or leave them in for the next usage. This embodiment may include a of variety calibration scale 24 assemblies of specialized pre-determined designs to provide the user with interchangeable scales customized for their point in recovery.

FIGS. 12A-12D Description—Additional Embodiment—Contour Version

In FIG. 12A, the outer surface and shape of casing 20 forms a grip contour 33A, to securely fit the user's hand and increase grip. There are various possibilities with regard to the grip contour 33A, which may comprise any suitable structure to accomplish this goal, including having one side flat and one side contoured (FIG. 12B), having one or more grooves, having patterns etched or embossed into the surface of casing 20, or having materials affixed to the surface of casing 20 to reduce slippage (not shown). Further possibilities include forming a handle 34 as part of casing 20 (FIG. 12C), or including handle 34 as a separate element (not shown) such that it is releasably or fixedly attached to casing 20. As illustrated in FIG. 12D, a further possibility includes both the handle 34 and a grip contour 33A.

FIG. 12E Operation—Additional Embodiment—Contour Version

The use of the embodiment is largely similar to the operation described in the above operation section A-F. When operating this embodiment, the user fits his or her hand into contour 33A. This helps guide the user's hand in place and obtain the proper position and orientation for use. It further helps provide the user with a steady grip of the embodiment and enhances the device's ability to fit comfortably and securely against the user's palm.

The inclusion of handle 34 on an embodiment provides an alternate operation for a measurement of pronation. In this case, the user grips handle 34 as illustrated in FIG. 12E (the left hand is shown). In this position, the user's palm is pressed up against the outside of handle 34, and his or her fingers are wrapped around in the area in-between handle 34 and casing 20 (FIG. 12E). Then, the user rotates his or her forearm in the direction of arrow 28B. This rotation brings the hand into a palm-down posture, top 21 to point in a direction towards the inside of the body, and bottom 25 to point in a direction towards the outside of the body (not shown).

When the user has rotated his or her forearm until resistance is felt and no additional movement is possible, he or she obtains the range of motion measurement by viewing the ending position of fluid 23 on calibration scale 24 (not shown) as a visual indicator of the measurement. Due to the similarities of this operation to the other positions, the details are not repeated here for brevity.

FIG. 13 Description—Additional Embodiment—Adjustable Fluid Version

In FIG. 13, top 21 provides for the addition or removal of fluid 23 by including a casing opening protrusion 35A, a casing opening 35B, and a casing opening cover 35C. The casing opening protrusion 35A is an opening into casing 20 providing a location into which fluid 23 is added to or removed from opening 20. The casing opening cover 35C is configured to create a water-tight seal for the opening protrusion 35A.

Operation—Additional Embodiment—Adjustable Fluid Version

The use of the embodiment is largely similar the operation described in the above operation section A-F. When operating this embodiment, the user fills casing 20 with the desired level of fluid 23, using the casing opening 35B. When the desired level of fluid 23 is inside of casing 20, the user secures fluid 23 inside of casing 20 by adding casing opening cover 35C to the embodiment. Changing the level of fluid 23 is of particular importance if the embodiment includes a plurality of adjustable or releasable calibration scale 24 assemblies, which are designed to function with a pre-determined level of fluid 23.

FIG. 14A Description—Additional Embodiment—Top Protrusion Version

In FIG. 14A, the embodiment includes a top protrusion 36 releasably or fixedly attached to the top 21 of casing 20. The top protrusion 36 is configured to allow a user's hand to grip it. This embodiment includes similar elements as other embodiments (e.g., as illustrated in FIG. 1), however FIG. 14A does not show all of the elements for simplicity.

FIG. 14B Operation—Additional Embodiment—Top Protrusion Version

The use of the embodiment is largely similar to the operation described in the above operation sections A-F. When operating this embodiment, the user has the choice of gripping the embodiment directly on casing 20 (not shown), or on the top protrusion 36 (FIG. 14B). The user's left hand is illustrated gripping top protrusion 36 in FIG. 14B.

One possible configuration for this embodiment includes the use of the adjustable calibration scale 24 assembly (FIG. 10) or the removable calibration scale 24 assembly (FIGS. 11A and 11B). This configuration is beneficial due to the varying ways of gripping the embodiment, such as gripping on casing 20 (not shown), or gripping top protrusion 36 (FIG. 14B).

The embodiment illustrated in FIG. 14A enables the user to obtain a measurement of pronation (palm down) by gripping the top protrusion 36 as illustrated in FIG. 14B. In this illustration, the palm side of the user's hand is facing the inside of the body and the thumb is at the top of the fingers. In this position, top 21 is facing the floor, and bottom 25 is facing the ceiling. Then, the user rotates his or her forearm to bring the hand into the palm down (pronation) posture. As the user performs this rotation, fluid 23 reacts to gravitational force and changes its location along a calibration scale 24 assembly on casing 20 (not shown due it is similarity with other embodiments). The user then obtains the range of motion measurement for pronation by viewing the ending position of fluid 23 on a calibration scale 24 assembly as a visual indicator of the measurement (not shown).

CONCLUSION, RAMIFICATIONS, AND SCOPE

Accordingly, the reader will see that the device of the various embodiments is unique in that it provides a portable, hand-held, inexpensive system to assess the joint range of motion of the wrist and forearm. The device does not require complex training to use and can be used whenever and wherever it is convenient. The device engages and motivates the user, and is multifunctional due to its suitability for exercise and stretching purposes. Furthermore, the device has the additional advantages in that:

The device will have a lower manufacturing cost, and a lower purchase cost than most other range of motion measurement devices, which will enable a person to buy it for their personal use.

It is so easy to use, the patient may even use it several times a day, to obtain a measurement of their range of motion. This self assessment in-between appointments with a medical practitioner provides valuable insight on the effectiveness of the user's home based therapeutic regimen. It provides both knowledge of their recovery process and a positive motivating influence to continue working towards recovery.

The device has a surface that can be written on, permitting users to customize and personalize it during their recovery as they track their own progress.

The calibration scale has user-friendly features, such as milestones that provide useful benchmarks for users. In addition, milestones that correlate to the range of motion required for different functional activities (e.g., eating, activities of daily living, etc.) helps to engage users in their recovery process and to help them understand it. Further, the presence of color on the calibration scales helps users to easily understand and remember where they are in the healing process.

It provides visual feedback during exercise and stretching, unlike a dumbbell or an elastic band.

It permits a person to use it in the non-affected hand, to compare their normal level of range of motion with the hand that is improving. This can serve as a baseline, as well as motivation to the user to work towards having two fully functioning hands.

Although the description above contains many specificities, these should not be construed as limiting the scope of the embodiment but as merely providing illustration of some of the presently preferred embodiments. Many other variations are possible. For example:

An embodiment can have instructive items or other marks arranged on the device. For example, marks can provide visual cues to aid users with finger and hand positioning (to increase repeatability), or arrows can provide visual reference to users on the movements involved in range of motion measurements.

An embodiment can have different size elements to customize it for different hand sizes, such as for use with a child or an adult.

An embodiment can include a slider marker to enable users to mark their current joint range of motion.

An embodiment can have a different shape, other than being largely cylindrical.

An embodiment can have weight acceptors so that a user may attach and detach additional weight to increase or decrease the resistance the embodiment provides for exercise.

An embodiment can have an adjustable strap to help the user grip the device during use.

An embodiment can have one or more gravity based pendulum protractors or circular bulls-eye style levels affixed to the casing (e.g., on the top or bottom), to measure joint range of motion.

An embodiment can have one or more of the following: a digital display, an audio indicator that gives an audible cue when a milestone is reached, a non-fluid based leveling element (e.g., electronic level, etc.). The fluid may be eliminated if not necessary.

The illustrations and examples provided herein are for explanatory purposes and are not intended to limit the scope of the appended claims. On the contrary, the invention is intended to cover alternatives, modifications and equivalents, which may be included within the sprit and scope of the invention as defined by the appended claims. Accordingly, the scope of the embodiment should be determined by the appended claims and their legal equivalents, rather than by the examples given.

What is claimed is:

1. A method of measuring joint range of motion, comprising:
   a) providing a casing of substantially cylindrical shape, of sufficient size to accommodate the grip of a human hand, and with walls fabricated of a water-tight and substantially transparent material, and having a top and a bottom,
   b) providing a fluid inside of said casing,
   c) providing a plurality of calibration means for providing predefined graduated incremental scale of values when mounted along the length of and around the circumference of said casing,
   d) selecting a human arm as the subject for the measurement activities,
   e) bending a elbow of said human arm to 90 degrees and holding said elbow next to the human's body,
   f) gripping said casing in a pre-determined location with said human hand of said human arm,
   g) performing various bending and rotation movements with said human hand gripping said casing, which causes said fluid to simultaneously shift locations within said casing due to the downward pull of gravity,
   h) viewing the point of intersection of said fluid on said calibration means at the point where no additional movement of said human hand is possible,
   whereby a measurement of joint range of motion is obtained.

2. A method of assessing joint range of motion according to claim 1, further comprising:
   a) gripping said casing with said top pointing up and with the palm side of said human hand facing the inside of the human's body,
   b) rotating said human hand of said human arm into the palm up position,
   c) viewing the point of intersection of said fluid on said calibration means at the point where no additional movement of said human hand is possible,
   whereby a measurement of supination is obtained.

3. A method of assessing joint range of motion according to claim 1, further comprising
   a) gripping said casing with said top pointed towards the inside of the human body and with the palm side of said human hand facing the floor,
   b) bending the wrist of said human arm downwards such that the fingers of said human hand curl to a position closer to the human's lower body,
   c) viewing the point of intersection of said fluid on said calibration means at the point where no additional movement of said human hand is possible,
   whereby a measurement of flexion in the palm down position is obtained.

4. A method of assessing joint range of motion according to claim 1, further comprising:
   a) gripping said casing with said top pointed towards the inside of the human body and with the palm side of said human hand facing the floor,
   b) bending the wrist of said human arm upwards such that the fingers of said human hand curl to a position closer to the human's upper body,
   c) viewing the point of intersection of said fluid on said calibration means at the point where no additional movement of said human hand is possible,
   whereby a measurement of extension is obtained.

5. A method of assessing joint range of motion according to claim 1, further comprising:
   a) straightening the elbow of the selected arm and holding the arm down next to the lower body such that the palm side of the hand is facing the body,
   b) gripping said casing with said casing's top pointing forwards,
   c) bending the wrist of said human arm forwards (fingers towards radius bone) and backwards (fingers toward ulnar bone),
   d) viewing the point of intersection of said fluid on said calibration means at the point where no additional movement of said human hand is possible,
   whereby a measurement of radial deviation and ulnar deviation is obtained.

6. A method of assessing joint range of motion according to claim 1, further comprising:
   a) performing pre-determined exercise movements, including bending and rotation actions, for a defined number of repetitions, with said human hand gripping said casing,
   whereby exercise is achieved by repeating the exercise movements until the exercise is complete.

7. A method of assessing joint range of motion according to claim 1, further comprising:
   a) performing pre-determined stretching movements, including bending and rotation motions, for a defined number of repetitions and duration, with said human hand gripping said casing, and with a second human hand assisting to deepen the stretch,
   whereby stretching is achieved by increasing the joint range of motion.

* * * * *